(12) United States Patent
Marubashi

(10) Patent No.: US 11,213,072 B2
(45) Date of Patent: Jan. 4, 2022

(54) POWER SUPPLY UNIT FOR AEROSOL INHALER

(71) Applicant: JAPAN TOBACCO INC., Tokyo (JP)

(72) Inventor: Keiji Marubashi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/076,875

(22) Filed: Oct. 22, 2020

(65) Prior Publication Data

US 2021/0120882 A1    Apr. 29, 2021

(30) Foreign Application Priority Data

Oct. 24, 2019   (JP) .............................. JP2019-193705

(51) Int. Cl.
*A24F 40/57* (2020.01)
*A24F 40/53* (2020.01)
(Continued)

(52) U.S. Cl.
CPC .............. *A24F 40/57* (2020.01); *A24F 40/10* (2020.01); *A24F 40/53* (2020.01); *H02J 7/0063* (2013.01);
(Continued)

(58) Field of Classification Search
CPC ......... A61M 15/06; A24F 40/53; A24F 40/57; H02J 7/0063
See application file for complete search history.

(56) References Cited

U.S. PATENT DOCUMENTS

RE46,543 E   *   9/2017   Trevor-Wilson .... A61M 16/109
2004/0168513 A1       9/2004   Aoshima et al.
(Continued)

FOREIGN PATENT DOCUMENTS

CN         208354611 U     1/2019
CN         110250580 A     9/2019
(Continued)

OTHER PUBLICATIONS

Decision to Grant a Patent received for Japanese Patent Application No. 2019-193705, dated Jan. 28, 2020, 5 pages including English Translation.
(Continued)

*Primary Examiner* — Anthony Calandra
(74) *Attorney, Agent, or Firm* — Xsensus LLP

(57) ABSTRACT

A power supply unit for an aerosol inhaler includes: a first element connected in series to a load and having a first electric resistance value; a second series circuit including a second element having a second electric resistance value and a third element connected in series to the second element and having a third electric resistance value, and connected in parallel with a first series circuit including the load and the first element; and an operational amplifier in which one of a non-inverting input terminal and an inverting input terminal is connected to the first series circuit, and the other of the non-inverting input terminal and the inverting input terminal is connected to the second series circuit. Each of the first to third electric resistance values is larger than the electric resistance value of the load at a normal temperature or a temperature in a predetermined temperature range.

15 Claims, 11 Drawing Sheets

(51) Int. Cl.
*H02J 7/00* (2006.01)
*A24F 40/10* (2020.01)
*H02J 50/10* (2016.01)
*A24F 40/90* (2020.01)

(52) U.S. Cl.
CPC ............. *A24F 40/90* (2020.01); *H02J 7/0045* (2013.01); *H02J 50/10* (2016.02)

(56) References Cited

U.S. PATENT DOCUMENTS

| | | | |
|---|---|---|---|
| 2016/0143359 A1* | 5/2016 | Xiang | H05B 1/0227 |
| | | | 392/387 |
| 2016/0174611 A1* | 6/2016 | Monsees | H05B 3/04 |
| | | | 392/387 |
| 2017/0095005 A1* | 4/2017 | Monsees | H05B 1/0244 |
| 2018/0043114 A1 | 2/2018 | Bowen et al. | |
| 2019/0059446 A1 | 2/2019 | Kessler et al. | |
| 2020/0022416 A1* | 1/2020 | Alarcon | A24F 40/53 |
| 2020/0128874 A1* | 4/2020 | Atkins | A24F 40/44 |
| 2020/0296800 A1 | 9/2020 | Ueda et al. | |
| 2020/0352249 A1* | 11/2020 | Achtien | A24F 40/50 |
| 2020/0375258 A1* | 12/2020 | Mizuguchi | H05B 1/0244 |

FOREIGN PATENT DOCUMENTS

| | | |
|---|---|---|
| JP | 61-18594 U | 2/1986 |
| JP | 5-55491 U | 7/1993 |
| JP | 3975440 B2 | 9/2007 |
| JP | 2017-501805 A | 1/2017 |
| JP | 2019-509733 A | 4/2019 |
| JP | 2019-101645 A | 6/2019 |
| KR | 2019-0022360 A | 3/2019 |
| WO | 2015/100361 A1 | 7/2015 |
| WO | 2018/019533 A1 | 2/2018 |
| WO | 2019/107446 A1 | 6/2019 |

OTHER PUBLICATIONS

Office Action dated Feb. 25, 2021, in corresponding Korean patent Application No. 10-2020-0137161, 12 pages.
European search report dated Mar. 11, 2021, in corresponding European patent Application No. 20203320.5, 3 pages.
Chinese Office Action dated Jul. 26, 2021 in Chinese Application No. 202011145557.6.

* cited by examiner

POWER SUPPLY UNIT FOR AEROSOL INHALER

CROSS-REFERENCE TO RELATED APPLICATIONS

This application is based on and claims priority under 35 USC 119 from Japanese Patent Application No. 2019-193705 filed on Oct. 24, 2019, the contents of which are incorporated herein by reference.

TECHNICAL FIELD

The present disclosure relates to a power supply unit for an aerosol inhaler.

BACKGROUND ART

JP-T-2017-501805 describes a circuit configured to measure a resistance value of a heater in a device that generates an inhalable aerosol.

Since the aerosol inhaler is used by a user holding the aerosol inhaler in his or her mouth, temperature control of the heater used to generate the aerosol is important.

On the other hand, increase of aerosol generation efficiency is also required. JP-T-2017-501805 describes measurement of the resistance value of the heater, but does not disclose a specific configuration thereof.

An object of the present disclosure is to provide a power supply unit for an aerosol inhaler capable of detecting a temperature of a load used to generate an aerosol with high accuracy while improving aerosol generation efficiency.

SUMMARY OF INVENTION

The present disclosure provides a power supply unit for an aerosol inhaler having a power supply capable of performing discharge to a load, which heats an aerosol generation source and whose temperature and electric resistance value have a correlation. The power supply unit for the aerosol inhaler includes: a first element connected in series to the load and having a first electric resistance value; a second series circuit including a second element having a second electric resistance value and a third element connected in series to the second element and having a third electric resistance value, and connected in parallel with a first series circuit including the load and the first element; and an operational amplifier in which one of a non-inverting input terminal and an inverting input terminal is connected to the first series circuit, and the other of the non-inverting input terminal and the inverting input terminal is connected to the second series circuit. Each of the first electric resistance value, the second electric resistance value and the third electric resistance value is larger than the electric resistance value of the load at a normal temperature or a temperature in a predetermined temperature range.

The present disclosure also provides a power supply unit for an aerosol inhaler having a power supply capable of performing discharge to a load, which heats an aerosol generation source and whose temperature and electric resistance value have a correlation. The power supply unit for the aerosol inhaler includes: a first element connected in series to the load and having a first electric resistance value; a second series circuit including a second element having a second electric resistance value and a third element connected in series to the second element and having a third electric resistance value, and connected in parallel with a first series circuit including the load and the first element to the power supply; and an operational amplifier in which one of a non-inverting input terminal and an inverting input terminal is connected to the first series circuit, and the other of the non-inverting input terminal and the inverting input terminal is connected to the second series circuit. When the load is at least one of a normal temperature or a normal temperature in a predetermined temperature range, a first temperature at which an aerosol can be generated, and a second temperature that can be reached only when the aerosol generation source is exhausted, a first resistance ratio, which is a value obtained by dividing an electric resistance value of a high potential side element in a circuit connected to the inverting input terminal of the operational amplifier among the first series circuit and the second series circuit by an electric resistance value of a low potential side element, is larger than a second resistance ratio, which is a value obtained by dividing an electric resistance value of a high potential side element in a circuit connected to the non-inverting input terminal of the operational amplifier among the first series circuit and the second series circuit by an electric resistance value of a low potential side element.

DESCRIPTION OF EMBODIMENTS

Figure 1:
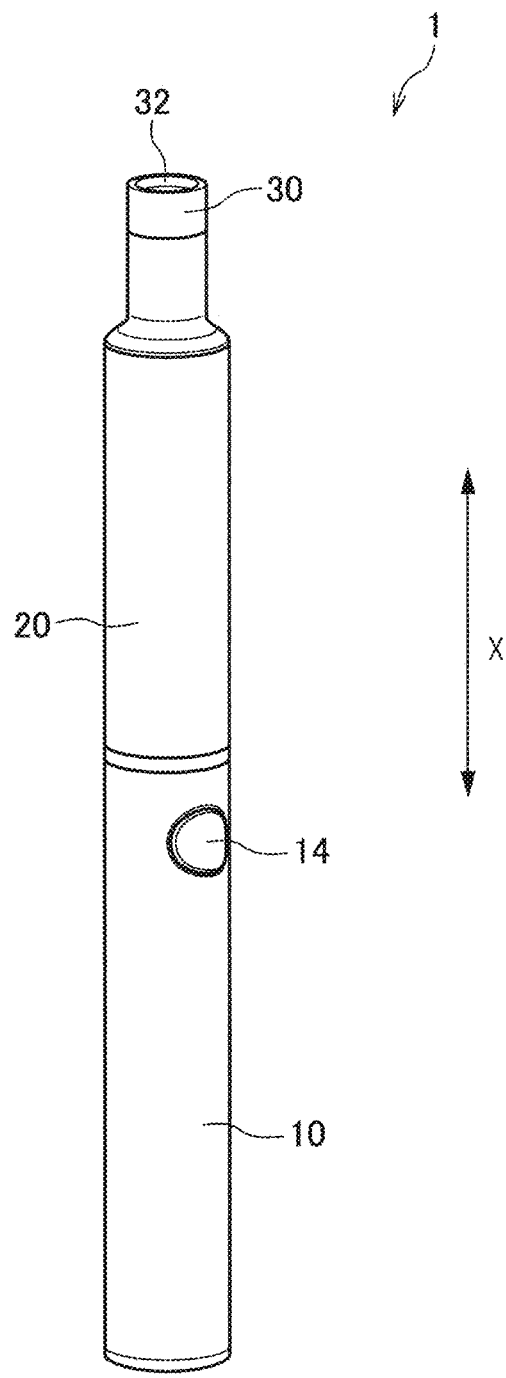
FIG. 1 is a perspective view of an aerosol inhaler equipped with a power supply unit according to an embodiment of the present disclosure.
Figure 2:
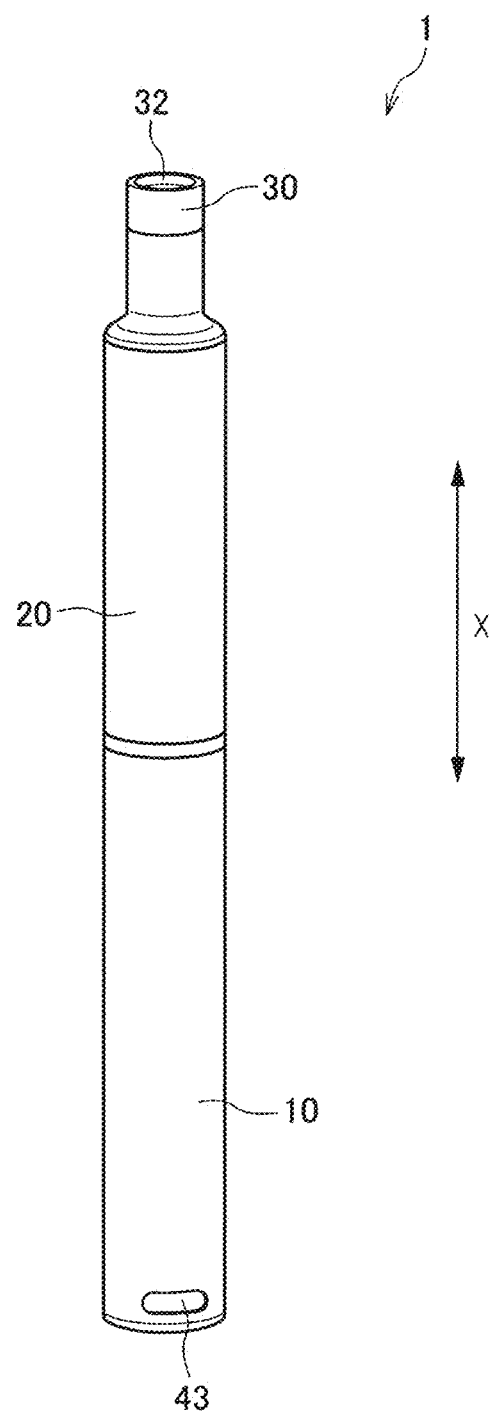
FIG. 2 is another perspective view of the aerosol inhaler shown in FIG. 1.

Hereinafter, a power supply unit for an aerosol inhaler according to an embodiment of the present disclosure will be described, but first, the aerosol inhaler equipped with the power supply unit will be described with reference to FIGS. 1 and 2.

(Aerosol Inhaler)

An aerosol inhaler 1 is a device for inhaling an aerosol to which a flavor is added without combustion, and has a rod shape extending along a predetermined direction (hereinafter referred to as a longitudinal direction X). The aerosol inhaler 1 is provided with a power supply unit 10, a first cartridge 20 and a second cartridge 30 in this order along the longitudinal direction X. The first cartridge 20 is attachable to and detachable from the power supply unit 10. The second cartridge 30 is attachable to and detachable from the first cartridge 20. In other words, the first cartridge 20 and the second cartridge 30 are replaceable.

(Power Supply Unit)

As shown in FIGS. 3, 4, 5 and 6, the power supply unit 10 according to the present embodiment accommodates a power supply 12, a charging IC 55A, a micro controller unit (MCU) 50, and various sensors such as an intake sensor 15 inside a cylindrical power supply unit case 11. The power supply 12 is a rechargeable secondary battery, an electric double layer capacitor or the like, and is preferably a lithium ion secondary battery. An electrolyte of the power supply 12 may be one of a gel electrolyte, an electrolytic solution, a solid electrolyte, an ionic liquid, or a combination thereof.

Figure 4:
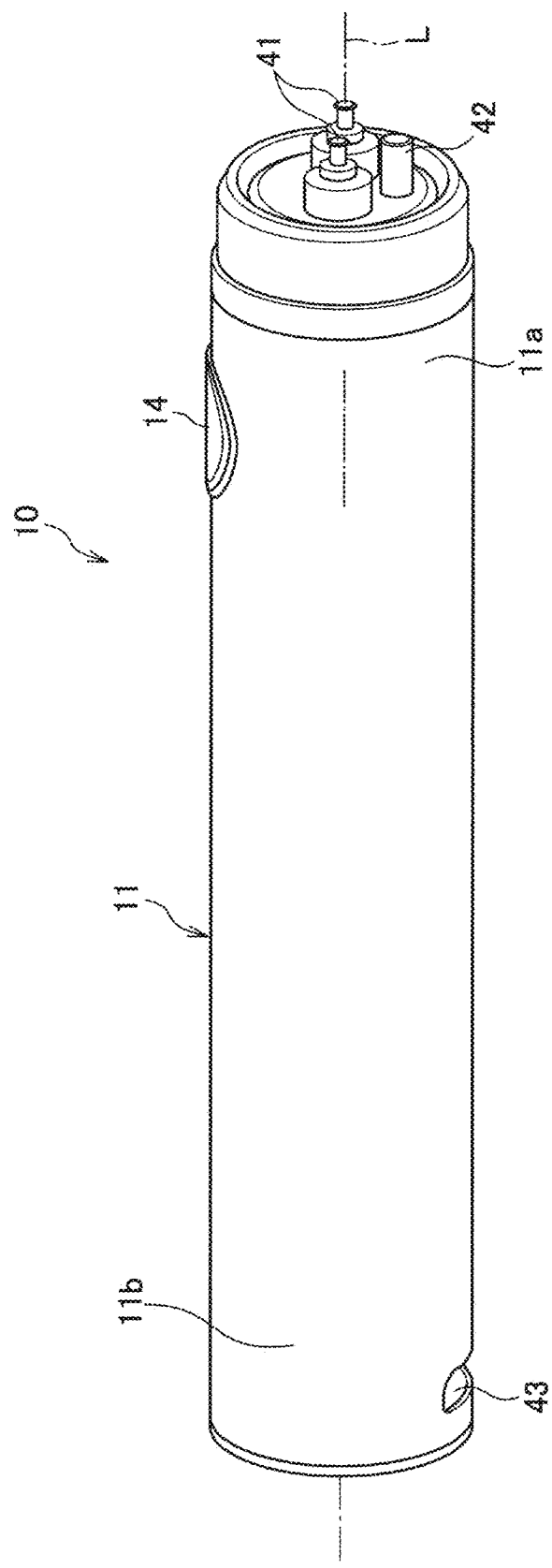
FIG. 4 is a perspective view of the power supply unit in the aerosol inhaler shown in FIG. 1.

As shown in FIG. 4, discharge terminals 41 are provided on a top portion 11a located on one end side (a first cartridge 20 side) of the power supply unit case 11 in the longitudinal direction X. The discharge terminals 41 are provided so as to protrude from an upper surface of the top portion 11a toward the first cartridge 20, and are configured to be electrically connectable to a load 21 of the first cartridge 20.

An air supply portion 42 that supplies air to the load 21 of the first cartridge 20 is provided on the upper surface of the top portion 11a in vicinity of the discharge terminals 41.

A charging terminal 43 that is electrically connectable to an external power supply (not shown) capable of charging the power supply 12 is provided on a bottom portion 11b located on the other end side (a side opposite to the first cartridge 20) of the power supply unit case 11 in the longitudinal direction X. The charging terminal 43 is provided on a side surface of the bottom portion 11b, and for example, at least one of a USB terminal, a microUSB terminal and a Lightning (registered trademark) terminal can be connected.

The charging terminal 43 may be a power reception unit capable of wirelessly receiving power transmitted from the external power supply. In such a case, the charging terminal 43 (the power reception unit) may be constituted by a power reception coil. A method of non-contact power transfer (wireless power transfer) may be an electromagnetic induction type or a magnetic resonance type. The charging terminal 43 may be the power reception unit capable of receiving the power transmitted from the external power supply without contact. As another example, at least one of the USB terminal, the microUSB terminal and the Lightning terminal can be connected to the charging terminal 43, and the charging terminal 43 may include the power reception unit described above.

Figure 3:
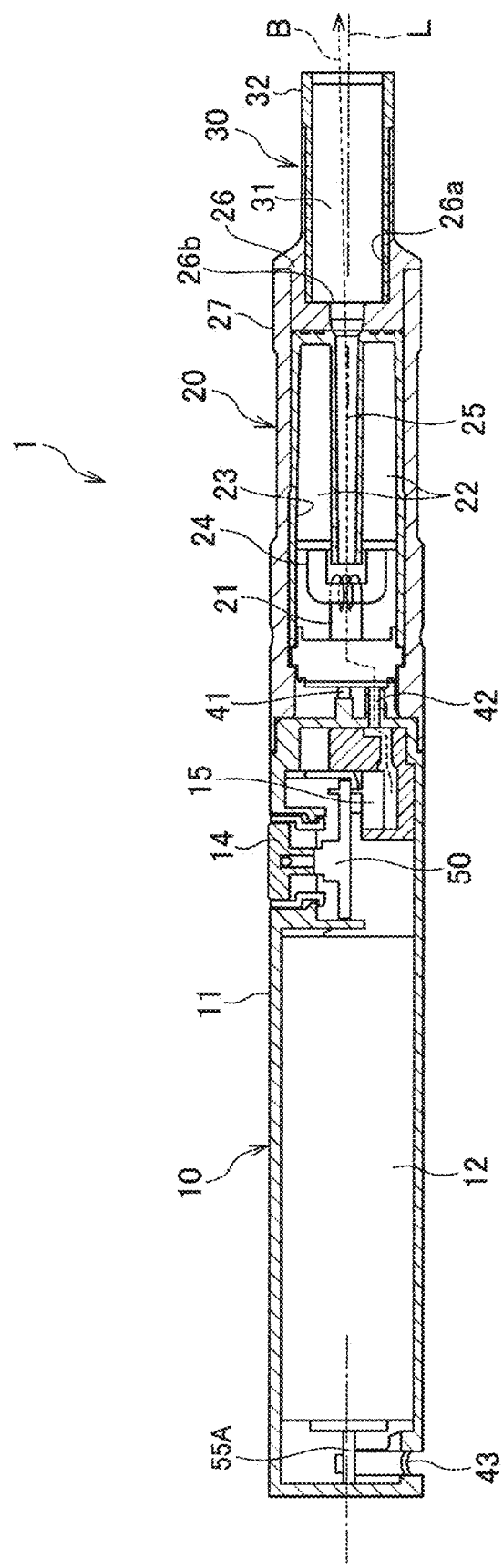
FIG. 3 is a cross-sectional view of the aerosol inhaler shown in FIG. 1.

The power supply unit case 11 is provided with a user-operable operation unit 14 on the side surface of the top portion 11a so as to face a side opposite to the charging terminal 43. More specifically, the operation unit 14 and the charging terminal 43 have a point-symmetrical relationship with respect to an intersection of a straight line connecting the operation unit 14 and the charging terminal 43 and a center line of the power supply unit 10 in the longitudinal direction X. The operation unit 14 includes a button type switch, a touch panel and the like. As shown in FIG. 3, the intake sensor 15 that detects a puff operation is provided in vicinity of the operation unit 14.

The charging IC 55A is disposed close to the charging terminal 43, and controls charging of the power supply 12 with the power input from the charging terminal 43. The charging IC 55A may be disposed in vicinity of the MCU 50.

Figure 5:
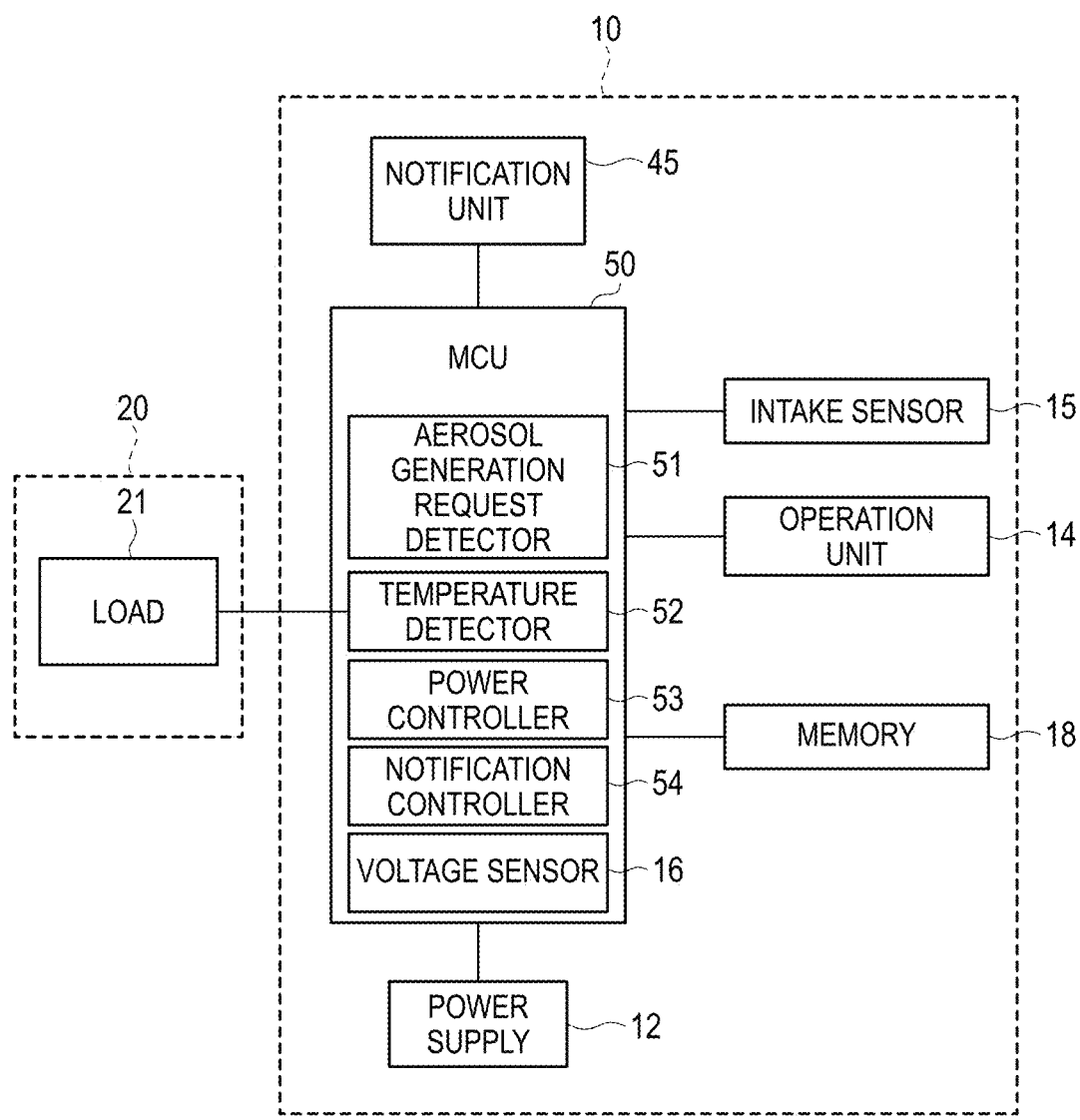
FIG. 5 is a block diagram showing a main part configuration of the power supply unit in the aerosol inhaler shown in FIG. 1.

As shown in FIG. 5, the MCU 50 is connected to various sensor devices such as the intake sensor 15 that detects the puff (intake) operation, the operation unit 14, a notification unit 45 described below, and a memory 18 that stores the number of puff operations or energization time to the load 21. The MCU 50 performs various controls of the aerosol inhaler 1. The MCU 50 is specifically constituted mainly by a processor 55 (see FIG. 7) described below, and further includes a storage medium such as a random access memory (RAM) required for an operation of the processor 55 and a read only memory (ROM) that stores various types of information. More specifically, the processor in the present specification is an electric circuit in which circuit elements such as semiconductor elements are combined.

The MCU 50 includes a voltage sensor 16 that measures a power supply voltage of the power supply 12. The voltage sensor 16 may include an operational amplifier 56 and an ADC 57 described below. In the MCU 50, an output signal of the voltage sensor 16 is input to the processor 55. Instead of the present embodiment, the voltage sensor 16 may be provided outside the MCU 50 and connected to the MCU 50.

The power supply unit case 11 is provided therein with an air intake port (not shown) that takes in outside air. The air intake port may be provided around the operation unit 14, or may be provided around the charging terminal 43.

(First Cartridge)

As shown in FIG. 3, The first cartridge 20 includes, in a cylindrical cartridge case 27, a reservoir 23 that stores an aerosol source 22, an electric load 21 that atomizes the aerosol source 22, a wick 24 that draws the aerosol source from the reservoir 23 to the load 21, an aerosol flow path 25 in which the aerosol generated by atomization of the aerosol source 22 flows toward the second cartridge 30, and an end cap 26 that accommodates a part of the second cartridge 30.

The reservoir 23 is partitioned and formed so as to surround a periphery of the aerosol flow path 25, and stores the aerosol source 22. A porous body such as a resin web or cotton may be accommodated in the reservoir 23, and the aerosol source 22 may be impregnated in the porous body. In the reservoir 23, the porous body on the resin web or cotton may not be contained, and only the aerosol source 22 may be stored. The aerosol source 22 includes a liquid such as glycerin, propylene glycol or water.

The wick 24 is a liquid holding member that draws the aerosol source 22 from the reservoir 23 to the load 21 by utilizing a capillary phenomenon. The wick 24 is formed of, for example, glass fiber or porous ceramic.

The load 21 atomizes the aerosol source 22 by heating the aerosol source 22 without combustion with the power supplied from the power supply 12 via the discharge terminals 41. The load 21 is formed of an electric heating wire (a coil) wound at a predetermined pitch.

The load 21 may be any element that can perform atomization by heating the aerosol source 22 to generate the aerosol. The load 21 is, for example, a heating element. Examples of the heating element include a heating resistor, a ceramic heater and an induction heating type heater. Hereinafter, an electric resistance value of the load 21 will be referred to as an electric resistance value $R_H$.

As the load 21, a load whose temperature and electric resistance value have a correlation is used. As the load 21, a load having a positive temperature coefficient (PTC) characteristic in which the electric resistance value is also increased as the temperature is increased is used. The PTC characteristic is also referred to as a positive resistance temperature coefficient characteristic.

A coefficient indicating an amount of change in the electric resistance value of the load 21 with respect to an amount of change in the temperature of the load 21 is referred to as a resistance temperature coefficient α [ppm (parts per million)/° C.]. The resistance temperature coefficient α is expressed by the following formula (F0), in which the temperature of the load 21 is T, a reference temperature is $T_{REF}$, and a reference electric resistance value is $R_{REF}$.

[Equation 1]

$$\alpha \ [\text{ppm}/^\circ \text{C.}] = \frac{R_H - R_{REF}}{R_{REF}} \cdot \frac{1}{T - T_{REF}} \cdot 10^6 \quad (F0)$$

The aerosol flow path 25 is provided on a downstream side of the load 21 and on a center line L of the power supply unit 10. The end cap 26 includes a cartridge accommodation portion 26a that accommodates a part of the second cartridge 30, and a communication path 26b that allows the aerosol flow path 25 and the cartridge accommodation portion 26a to communicate with each other.

(Second Cartridge)

The second cartridge 30 stores a flavor source 31. The second cartridge 30 is detachably accommodated in a cartridge accommodation portion 26a provided in the end cap 26 of the first cartridge 20. An end portion of the second cartridge 30 on the side opposite to the first cartridge 20 is a suction port 32 for a user. The suction port 32 is not limited to being integrally formed with the second cartridge 30, but may be configured to be attachable to and detachable from the second cartridge 30. By configuring the suction port 32 separately from the power supply unit 10 and the first cartridge 20 in this way, the suction port 32 can be kept hygienic.

The second cartridge 30 imparts a flavor to the aerosol by passing the aerosol generated by atomizing the aerosol source 22 by the load 21 through the flavor source 31. As a raw material piece constituting the flavor source 31, chopped tobacco or a molded product obtained by molding a tobacco raw material into particles can be used. The flavor source 31 may be formed of a plant other than tobacco (for example, mint, Chinese herb or herb). The flavor source 31 may be provided with a fragrance such as menthol.

In the aerosol inhaler 1 according to the present embodiment, the aerosol to which the flavor is added can be generated by the aerosol source 22, the flavor source 31 and the load 21. That is, the aerosol source 22 and the flavor source 31 constitute an aerosol generation source that generates the aerosol.

The aerosol generation source of the aerosol inhaler 1 is a portion that is replaced and used by the user. This portion is provided, for example, to the user as a set of one first cartridge 20 and one or more (for example, five) second cartridges 30.

In addition to a configuration in which the aerosol source 22 and the flavor source 31 are separated from each other, a configuration in which the aerosol source 22 and the flavor source 31 are integrally formed, a configuration in which the flavor source 31 is omitted and substances that may be included in the flavor source 31 are added to the aerosol source 22, or a configuration in which a drug or the like instead of the flavor source 31 is added to the aerosol source 22 may also be employed as the configuration of the aerosol generation source used in the aerosol inhaler 1.

In a case of the aerosol inhaler 1 including the aerosol generation source in which the aerosol source 22 and the flavor source 31 are integrally formed, for example, one or more (for example, 20) aerosol generation sources are provided as a set to the user.

In a case of the aerosol inhaler 1 including only the aerosol source 22 as the aerosol generation source, for example, one or more (for example, 20) aerosol generation sources are provided as a set to the user.

In the aerosol inhaler 1 configured as described above, as shown by an arrow B in FIG. 3, the air flowing in from the intake port (not shown) provided in the power supply unit case 11 passes through vicinity of the load 21 of the first cartridge 20 from the air supply portion 42. The load 21 atomizes the aerosol source 22 drawn from the reservoir 23 by the wick 24. The aerosol generated by atomization flows through the aerosol flow path 25 together with the air flowing in from the intake port, and is supplied to the second cartridge 30 via the communication path 26b. The aerosol supplied to the second cartridge 30 is given the flavor by passing through the flavor source 31, and is supplied to the suction port 32.

The aerosol inhaler 1 is provided with the notification unit 45 that notifies various types of information (see FIG. 5). The notification unit 45 may be configured by a light emitting element, may be configured by a vibration element, or may be configured by a sound output element. The notification unit 45 may be a combination of two or more elements among the light emitting element, the vibration element and the sound output element. The notification unit 45 may be provided in any of the power supply unit 10, the first cartridge 20 and the second cartridge 30, but is preferably provided in the power supply unit 10. For example, a periphery of the operation unit 14 is translucent, and is configured to emit light by a light emitting element such as an LED.

In the aerosol inhaler 1 according to the present embodiment, as a recommended temperature (an operation guarantee temperature) during use, a temperature range capable of generating a sufficient amount of the aerosol and ensuring safety of the power supply 12 is determined in advance. This temperature range is, for example, a range of −10° C. or higher and 45° C. or lower including a normal temperature (specifically, a temperature in a range of 5° C. to 35° C. defined by Japanese Industrial Standards). In the aerosol inhaler 1 according to the present embodiment, a temperature (a first temperature) of the load 21 capable of generating the aerosol from the aerosol generation source is set to a value higher than the above temperature range (for example, about 200° C.). In the aerosol inhaler 1 according to the present embodiment, a temperature (a second temperature) of the load 21 that can be reached only when heating of the load 21 is continued in a state where the aerosol generation source is exhausted is set to a value higher than the first temperature (for example, about 300° C.). The state where the aerosol generation source is exhausted means that a remaining amount of the aerosol generation source is zero or almost zero.

That is, in the aerosol inhaler 1, a temperature of the load 21 may vary in a range including the temperature range, the first temperature higher than the temperature range, and a second temperature higher than the first temperature (as a specific example, a range of −10° C. or higher and 300° C. or lower). This range is hereinafter referred to as a normal temperature range. Numerical values of the temperature range, the first temperature and the second temperature are examples, and are set to appropriate values according to features of a product and the like. The temperature range may not include the normal temperature, or may be the normal temperature itself (Electric Circuit)

A main part of an electric circuit of the power supply unit 10 will be described with reference to FIG. 6.

The power supply unit 10 has a main circuit configuration, and includes the power supply 12, the discharge terminals 41 configured such that the first cartridge 20 including the above load 21 is detachable, the MCU 50, a low drop out (LDO) regulator 60, a switch 61, a switch 62, a first element 63 having a first electric resistance value $R_1$, a second element 64 having a second electric resistance value $R_2$, and a third element 65 having a third electric resistance value $R_3$.

Each of the first element 63, the second element 64 and the third element 65 may be an element having an electric resistance value, for example, a resistor, a diode, a transistor or the like. In an example of FIG. 6, each of the first element 63, the second element 64 and the third element 65 is the resistor.

Switches 61, 62 are switching elements such as transistors that switch between interruption and conduction of a wiring path. In the example of FIG. 6, each of the switches 61, 62 is a normally-off type insulated gate bipolar transistor (IGBT) that is turned on (conducted) by receiving a high-level turn-on command signal supplied from the MCU 50 and turned off (cut off) by receiving a low-level turn-off command signal supplied from the MCU 50.

The LDO regulator 60 and the MCU 50 are connected in series to the power supply 12. The LDO regulator 60 steps down a voltage from the power supply 12 and outputs the voltage. The output voltage of the LDO regulator 60 (hereinafter referred to as a reference voltage $V_{REF}$) is supplied to the MCU 50 as an operation voltage of the MCU 50. For example, the LDO regulator 60 steps down a voltage of 4.2V from the power supply 12 to 3.7V and outputs the voltage. Among a main positive bus LU and a main negative bus LD, the main positive bus LU is a high potential side line, and the main negative bus LD is a low potential side line. The main positive bus LU may be the line having the highest potential in the electric circuit of the power supply unit 10. The main negative bus LD may be the line having the lowest potential in the electric circuit of the power supply unit 10.

The MCU 50 is connected to the LDO regulator 60 and the main negative bus LD connected to a negative electrode of the power supply 12. The MCU 50 is also connected to the switch 61 and the switch 62, and performs on and off control of the switch 61 and the switch 62.

In a state where the first cartridge 20 is attached to the power supply unit 10, the first element 63 and the load 21 are connected in series to form a first series circuit C1. The second element 64 and the third element 65 are connected in series to form a second series circuit C2. The first series circuit C1 and the second series circuit C2 are connected in parallel between the main positive bus LU and the main negative bus LD.

The first series circuit C1 and the second series circuit C2 are connected to the main positive bus LU and the main negative bus LD. Specifically, a collector of the switch 62 is connected to the main positive bus LU, and the first element 63 and the second element 64 are connected in parallel to an emitter of the switch 62. The load 21 and the third element 65 are connected in parallel to the main negative bus LD. The load 21 is connected to the first element 63, and the third element 65 is connected to the second element 64.

In this way, the first series circuit C1 has a configuration in which the first element 63 is a high potential side element and the load 21 is a low potential side element. The second series circuit C2 has a configuration in which the second element 64 is a high potential side element and the third element 65 is a low potential side element.

The first series circuit C1 is connected to the MCU 50. Specifically, the first series circuit C1 is connected to the MCU 50 between the first element 63 and the load 21.

The second series circuit C2 is connected to the MCU 50. Specifically, the second series circuit C2 is connected to the MCU 50 between the second element 64 and the third element 65.

The switch 61 is connected to the main positive bus LU and the first series circuit C1. Specifically, a collector of the switch 61 is connected to the main positive bus LU. An emitter of the switch 61 is connected to a position on a lower potential side than a node connected to the MCU 50 in the first series circuit C1 between the first element 63 and the load 21.

Figure 6:
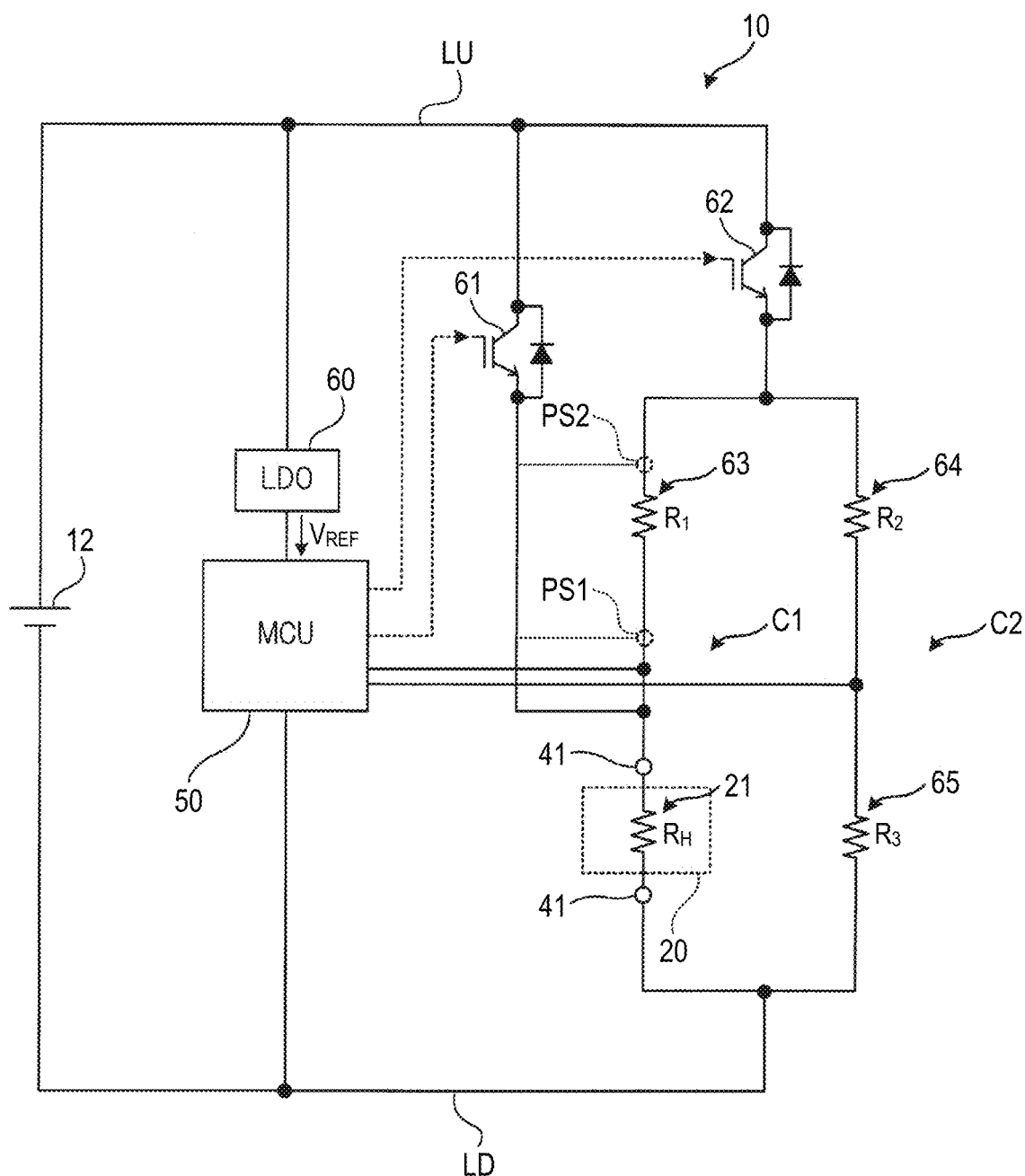
FIG. 6 is a circuit configuration of the power supply unit in the aerosol inhaler shown in FIG. 1.

The emitter of the switch 61 may be connected to a position PS1 on a higher potential side than the connection node of the first series circuit C1 with the MCU 50, as shown by a broken line in FIG. 6. The emitter of the switch 61 may be connected to a position PS2 on a higher potential side than the first element 63 in the first series circuit C1, as shown by a broken line in FIG. 6.

In the power supply unit 10 shown in FIG. 6, a circuit including the switch 61 and a wiring, connected between the main positive bus LU, and the first element 63 and the load 21 of the first series circuit C1, is hereinafter referred to as a heating circuit. A circuit including the switch 62 and a wiring, connecting the first series circuit C1 and the second series circuit C2 to the main positive bus LU, is hereinafter referred to as a first connection circuit. A circuit including a wiring, connecting the first series circuit C1 and the second series circuit C2 to the main negative bus LD, is hereinafter referred to as a second connection circuit.

(MCU)

Next, a configuration of the MCU 50 will be described in more detail. As shown in FIG. 5, the MCU 50 includes an aerosol generation request detector 51, a temperature detector 52, a power controller 53, and a notification controller 54, as functional blocks implemented by the processor executing programs stored in the ROM.

The aerosol generation request detector 51 detects an aerosol generation request based on an output result of the intake sensor 15. The intake sensor 15 is configured to output a value of a change in pressure (internal pressure) in the power supply unit 10 caused by suction of the user through the suction port 32. The intake sensor 15 is, for example, a pressure sensor that outputs an output value (for example, a voltage value or a current value) corresponding to the internal pressure that changes due to a flow rate of the air sucked from the intake port (not shown) toward the suction port 32 (that is, the puff operation of the user). The intake sensor 15 may be constituted by a condenser microphone or the like. The intake sensor 15 may output an analog value or a digital value converted from the analog value.

Although details will be described below, the temperature detector 52 detects the temperature of the load 21 based on an output signal of the first series circuit C1 and an output signal of the second series circuit C2 shown in FIG. 6. By turning on the switch 62 and turning off the switch 61, the temperature detector 52 causes a current to flow through each of the first series circuit C1 and the second series circuit C2, and detects the temperature of the load 21 based on the output signal of the first series circuit C1 and the output signal of the second series circuit C2 at that time.

The notification controller 54 controls the notification unit 45 to notify various types of information. For example, the notification controller 54 controls the notification unit 45 to notify a replacement timing of the second cartridge 30 according to detection of the replacement timing of the second cartridge 30. The notification controller 54 detects and notifies the replacement timing of the second cartridge 30 based on the cumulative number of the puff operations or the cumulative energization time to the load 21 stored in the memory 18. The notification controller 54 may notify not only the replacement timing of the second cartridge 30, but also a replacement timing of the first cartridge 20, a replacement timing of the power supply 12, a charging timing of the power supply 12 and the like.

In a state where one unused second cartridge 30 is set, when the puff operation is performed a predetermined number of times, or when the cumulative energization time to the load 21 by the puff operation reaches a predetermined value (for example, 120 seconds), the notification controller 54 determines that the second cartridge 30 has been used (that is, a remaining amount is zero or empty), and notifies the replacement timing of the second cartridge 30.

When it is determined that all the second cartridges 30 included in the set have been used, the notification controller 54 may determine that one first cartridge 20 included in the set has been used (that is, a remaining amount is zero or empty), and notify the replacement timing of the first cartridge 20.

When the aerosol generation request detector 51 detects the aerosol generation request, the power controller 53 controls discharge of the power supply 12 via the discharge terminals 41 by turning on or turning off the switches 61, 62. By turning off the switch 62 and turning on the switch 61, the power controller 53 causes a large current to flow through the load 21, and discharge to the load 21 is performed. When the discharge to the load 21 is performed in this way, more current flows through the load 21 than through the first element 63 in the first series circuit C1. As described below, since the first element 63, the second element 64 and the third element 65 each have a sufficiently large battery resistance value compared to the load 21, the current flowing through the first element 63 is zero or almost zero, and the current flows only through the load 21. Since the current flowing through the first element 63 is zero or almost zero, more current can flow from the power supply 12 to the load 21, and thus aerosol generation efficiency is improved.

Even in a configuration in which the emitter of the switch 61 is connected to the position PS1 in FIG. 6, when the discharge to the load 21 is performed, similarly, more current can flow through the load 21 than through the first element 63 in the first series circuit C1. In a configuration in which the emitter of the switch 61 is connected to the position PS2 in FIG. 6, when the discharge to the load 21 is performed, the current also flows through the first element 63 in the first series circuit C1. However, as described below, since an electric resistance value of the second series circuit C2 is larger than an electric resistance value of the load 21, more current can flow through the load 21. In any case, when the discharge to the load 21 is performed, the large current can flow through the load 21, and the load 21 can be efficiently heated.

(Configuration for Load Temperature Detection)

Figure 7:
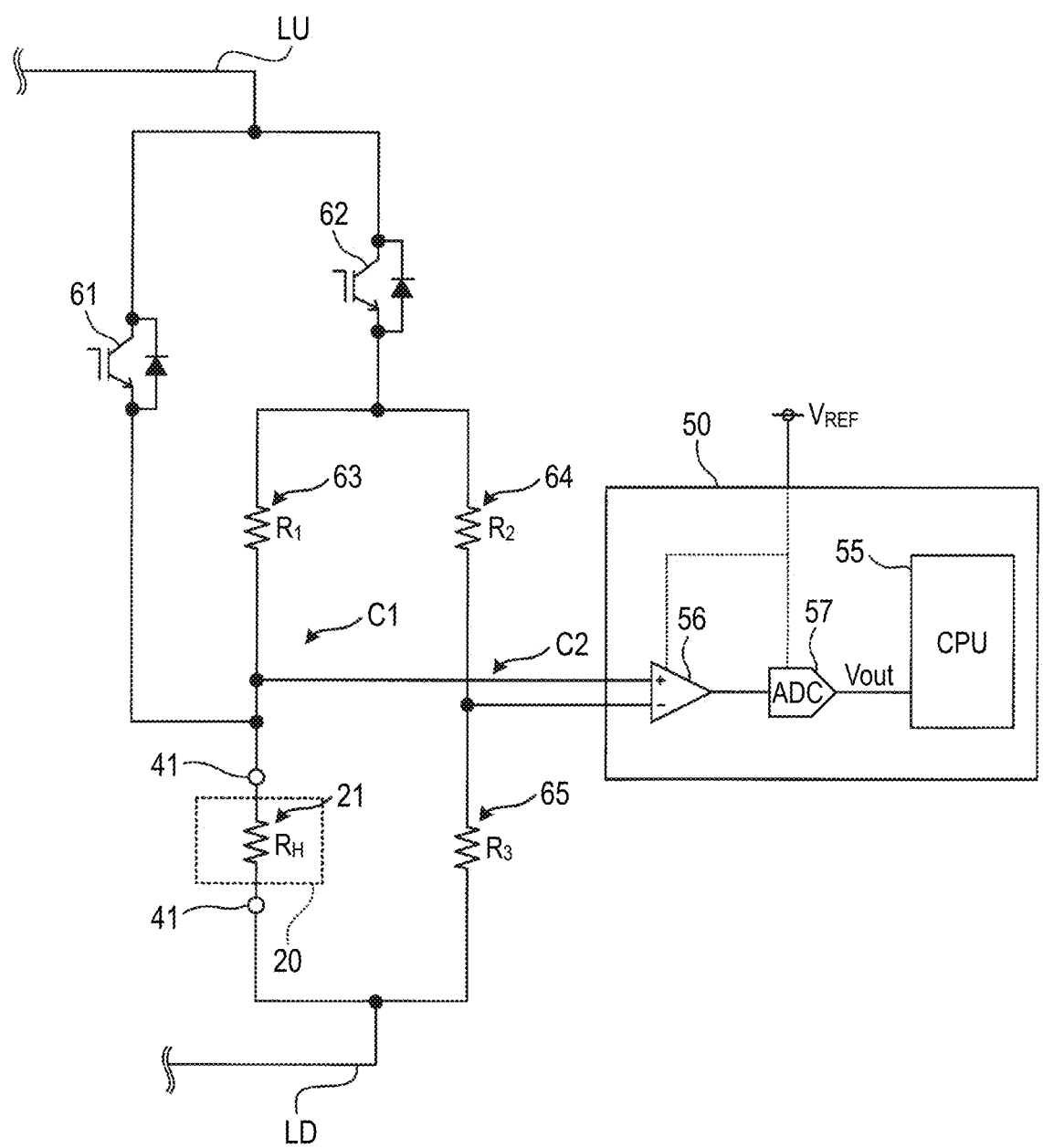
FIG. 7 is an enlarged view of a main part of the circuit configuration of the power supply unit shown in FIG. 6.

FIG. 7 is an enlarged view of a main part of a circuit configuration of the power supply unit 10 shown in FIG. 6.

As shown in FIG. 7, the MCU 50 includes the operational amplifier 56, the analog-digital converter (ADC) 57 and the processor 55. In all the embodiments, the operational amplifier 56 and the ADC 57 may be provided outside the MCU 50.

The operational amplifier 56 includes a non-inverting input terminal (+) and an inverting input terminal (−), and amplifies a difference value obtained by subtracting a voltage input to the inverting input terminal from a voltage input to the non-inverting input terminal by a predetermined amplification factor A and outputs the amplified difference value. This difference value changes when the electric resistance value of the load 21 changes with the temperature thereof. Similarly, an output signal of the operational amplifier 56 changes when the electric resistance value of the load 21 changes with the temperature thereof.

The operational amplifier 56 includes a pair of power supply terminals. As an example, a high potential side power supply terminal may be connected to the reference voltage $V_{REF}$. A low potential side power supply terminal is connected to a voltage lower than the reference voltage $V_{REF}$. As an example, the low potential side power supply terminal may be connected to the ground. When the power supply terminals of the operational amplifier 56 are connected in this way, an upper limit value of the difference value is a voltage (for example, $V_{REF}$) connected to the high potential side power supply terminal, and a lower limit value of the difference value is a voltage (for example, 0) connected to the low potential side power supply terminal. Therefore, even when the difference value exceeds the output value $V_{REF}$, the difference value is fixed to $V_{REF}$. Similarly, even when the difference value is lower than 0, the difference value is fixed to 0. In other words, in order to accurately obtain the electric resistance value and the temperature of the load 21 by using the output signal of the operational amplifier 56, the difference value is required to be set between $V_{REF}$ and 0.

The first series circuit C1 is connected to the non-inverting input terminal of the operational amplifier 56. Specifically, the non-inverting input terminal of the operational amplifier 56 is connected between the first element 63 and the load 21 in the first series circuit C1 and on a higher potential side than a connection node with the switch 61. The second series circuit C2 is connected to the inverting input terminal of the operational amplifier 56. Specifically, the inverting input terminal of the operational amplifier 56 is connected between the second element 64 and the third element 65 in the second series circuit C2.

The ADC 57 converts the output signal of the operational amplifier 56 into a digital signal and outputs the digital signal. As the ADC 57, an ADC having an N-bit resolution operated by the reference voltage $V_{REF}$ is used.

When the switch 62 is turned off and the switch 61 is turned on, a voltage $V_+$ input to the non-inverting input terminal of the operational amplifier 56 and a voltage $V_-$ input to the inverting input terminal of the operational amplifier 56, respectively, are expressed by the following formulas (F1), (F2), in which "V" is a voltage applied to the entire parallel circuit formed by the first series circuit C1 and the second series circuit C2 (In other words, a potential difference between the main positive bus LU and the main negative bus LD).

[Equations 2]

$$V_+ = \frac{R_H}{R_1 + R_H} \cdot V \quad (F1)$$

$$V_- = \frac{R_3}{R_2 + R_3} \cdot V \quad (F2)$$

Therefore, when the switch 62 is turned off and the switch 61 is turned on, the output signal of the operational amplifier 56 is expressed by the following formula (F3) with the amplification factor A and the formulas (F1), (F2). A portion of the formula (F3) excluding the amplification factor A indicates the difference value between a signal input to the non-inverting input terminal and a signal input to the inverting input terminal of the operational amplifier 56. Hereinafter, this difference value is also referred to as $V_{IN}$. The difference value $V_{IN}$ changes due to a change in the electric resistance value $R_H$ of the load 21. Hereinafter, an amount of change in the difference value $V_{IN}$ with respect to an amount of change in the electric resistance value $R_H$ of the load 21 will be referred to as $\Delta V_{IN}$ below. The amplification factor A may be any natural number of 1 or larger.

[Equation 3]

$$\begin{aligned}A \times (V_+ - V_-) &= A \cdot \frac{R_H}{R_1 + R_H} \cdot V - A \cdot \frac{R_3}{R_2 + R_3} \cdot V \\ &= A \cdot \frac{R_H \cdot (R_2 + R_3) - R_3 \cdot (R_1 + R_H)}{(R_1 + R_H) \cdot (R_2 + R_3)} \cdot V \\ &= A \cdot \frac{R_H \cdot R_2 - R_1 \cdot R_3}{(R_1 + R_H) \cdot (R_2 + R_3)} \cdot V\end{aligned} \quad (F3)$$

The temperature detector 52 serving as the functional block of the processor 55 acquires the output signal of the operational amplifier 56 when the switch 62 is turned off and the switch 61 is turned on. In the formula (F3), values other than the electric resistance value $R_H$ of the load 21 are known values. Therefore, the temperature detector 52 can derive the electric resistance value $R_H$ of the load 21 from the acquired output signal of the operational amplifier 56 and the formula (F3). The temperature detector 52 detects the temperature T of the load 21 based on the electric resistance value $R_H$ of the load 21 derived in this way and information on the PTC characteristic of the load 21 stored in advance in the ROM (for example, information on the reference temperature $T_{REF}$, the reference electric resistance value $R_{REF}$ corresponding to the reference temperature $T_{REF}$, and the resistance temperature coefficient α [ppm/° C.]).

Here, detection resolution of the temperature T of the load 21 by the temperature detector 52 will be considered.

A resolution Res [V/bit] by the N-bit ADC 57 to which the reference voltage $V_{REF}$ is input as a power supply is expressed by the following formula (F4).

[Equation 4]

$$Res\ [V/bit] = \frac{V_{REF}}{2^N} \quad (F4)$$

When the formula (F4) is rewritten, a temperature resolution Res [° C.] is expressed by the following formula (F5). $\Delta T_H$ ($\Delta R_H$) in the formula (F5) indicates an amount of change in the temperature T of the load 21 in accordance with the amount of change in the electric resistance value $R_H$ of the load 21. Therefore, the formula (F5) can be transformed into a formula (F6) by using a resistance temperature coefficient α [%] of the load 21. Note that in deriving the formula (F6), the resistance temperature coefficient α [ppm/° C.] is multiplied by $10^2$ and $10^{-6}$ in order to convert a unit of the resistance temperature coefficient α from [ppm/° C.] to [%].

[Equation 5]

$$Res\ [°\ C.] = \frac{\Delta T_H(\Delta R_H) \cdot Res[V/bit]}{\Delta V_{IN}} \quad (F5)$$

[Equation 6]

$$\begin{aligned}Res\ [°\ C.] &= \frac{1}{\alpha[\%]} \cdot \frac{1}{\Delta V_{IN}} \cdot Res\ [V/bit] \\ &= \frac{1}{\alpha[ppm/°\ C.] \times 10^2 \times 10^{-6}} \cdot \frac{1}{\Delta V_{IN}} \cdot Res\ [V/bit] \\ &= \frac{1}{\alpha[ppm/°\ C.] \times 10^{-4}} \cdot \frac{1}{\Delta V_{IN}} \cdot \frac{V_{REF}}{2^N}\end{aligned} \quad (F6)$$

As can be seen from the formula (F6), in order to increase a detection resolution of the temperature T of the load 21 by the temperature detector 52, the amount of change $\Delta V_{IN}$ in the difference value $V_{IN}$ of the operational amplifier 56, in other words, a multiplication value of the amplification factor A and the difference value $V_{IN}$ may be increased.

In the power supply unit 10 according to the present embodiment, as can be seen from the formula (F3), magnitudes of the signal input to the non-inverting input terminal and the signal input to the inverting input terminal of the operational amplifier 56 are significantly smaller than those when the inverting input terminal is connected to the ground. That is, the amount of change in the difference value $V_{IN}$ of the operational amplifier 56 is smaller than the amount of change in the electric resistance value $R_H$ of the load 21. On the other hand, the output signal of the operational amplifier 56 is input to the ADC 57, and the ADC 57 operates with the reference voltage $V_{REF}$. Therefore, the output signal of the operational amplifier 56 (an input signal of the ADC 57) is preferably equal to or lower than the reference voltage $V_{REF}$ in order for the ADC 57 to operate normally.

In the power supply unit 10 according to the present embodiment, the difference value $V_{IN}$ of the operational amplifier 56 can be set to a small value. Therefore, the amplification factor A can be set to a large value in a range in which the output signal of the operational amplifier 56 does not exceed the reference voltage $V_{REF}$. As a result, the multiplication value of the amplification factor A and the difference value $V_{IN}$ can be set to a large value, and the detection resolution of the temperature T can be increased.

(Preferable Conditions of Electric Resistance Values of Load, First Element, Second Element and Third Element)

When the temperature of the load 21 is detected, a current based on the voltage V flows through a bridge circuit including the first series circuit C1 and the second series circuit C2, and the bridge circuit itself serves as a heat source. Therefore, in order to prevent the Joule heat generated by the current flowing through the first series circuit C1 and the second series circuit C2 from affecting the temperature of the load 21, it is desirable to sufficiently increase an electric resistance value (a combined resistance value) of the entire bridge circuit including the first series circuit C1 and the second series circuit C2.

On the other hand, when the electric resistance value $R_H$ of the load 21 is set to a large value, an amount of power required to increase the temperature of the load 21 to a desired temperature is increased, or it takes time to increase the temperature of the load 21 to the desired temperature when the amount of power is suppressed. Therefore, it is desirable that the electric resistance value $R_H$ of the load 21 be minimized in order to increase the aerosol generation efficiency.

In order to increase the aerosol generation efficiency, the power supply unit 10 according to the present embodiment is configured to satisfy a resistance value condition that each of the first electric resistance value $R_1$ of the first element 63, the second electric resistance value $R_2$ of the second element 64, and the third electric resistance value $R_3$ of the third element 65 is larger than the electric resistance value $R_H$ of the load 21.

However, the electric resistance value $R_H$ is a value that changes with the temperature of the load 21. Therefore, the above resistance value condition is satisfied regardless of the temperature of the load 21 in the normal temperature range. As another embodiment, the electric resistance value $R_H$ may be configured such that the above resistance value condition is satisfied only when the load 21 is in a part of the normal temperature range. Specifically, the electric resistance value $R_H$ may be configured such that the above resistance value condition is satisfied when the load 21 is in the above temperature range, the above temperature range and the above first temperature, and the above temperature range and the above second temperature. With such a configuration, a width of options for the load 21 and other elements can be widened.

As described above, in order to accurately obtain the electric resistance value and the temperature of the load 21, the voltage $V_+$ input to the non-inverting input terminal of the operational amplifier 56 is required to be prevented from being lower than the voltage $V_-$ input to the inverting input terminal. Considering that the electric resistance value $R_H$ is the minimum in the formula (F3), the second electric resistance value $R_2$ is required to be larger than the third electric resistance value $R_3$. That is, in the power supply unit 10, the first electric resistance value $R_1$ is larger than the electric resistance value $R_H$, and the second electric resistance value $R_2$ is larger than the third electric resistance value $R_3$.

Here, a value obtained by dividing the first electric resistance value $R_1$ of the first element 63 serving as the high potential side element in the first series circuit C1, by the electric resistance value $R_H$ of the load 21 serving as the low potential side element in the first series circuit C1, is set to "n". A value obtained by dividing the second electric resistance value $R_2$ of the second element 64 serving as the high potential side element in the second series circuit C2, by the third electric resistance value $R_3$ of the third element 65 serving as the low potential side element in the second series circuit C2, is set to "m". In the power supply unit 10, since the first electric resistance value $R_1$ is larger than the electric resistance value $R_H$ and the second electric resistance value $R_2$ is larger than the third electric resistance value $R_3$, n and m are real numbers of 1 or larger. In this embodiment, m constitutes a first resistance ratio and n constitutes a second resistance ratio.

When n and m are defined in this way, "$R_1$" in the formula (F3) is "$n \cdot R_H$" and "$R_2$" is "$m \cdot R_3$". Therefore, the formula (F3) can be transformed as follows.

[Equation 7]

$$A \times (V_+ - V_-) = A \cdot \frac{R_H \cdot m \cdot R_3 - n \cdot R_H \cdot R_3}{(n + R_H + R_H) \cdot (m \cdot R_3 + R_3)} \cdot V \quad \text{(F7)}$$

$$= A \cdot \frac{R_H \cdot m \cdot R_3 - n \cdot R_H \cdot R_3}{(n+1) \cdot R_H \cdot (m+1) \cdot R_3} \cdot V$$

$$= A \cdot \frac{m - n}{(n+1) \cdot (m+1)} \cdot V$$

In the formula (F7), since a product of n and m in a denominator is strong, as n and m are larger, in other words, as $R_1$ and $R_2$ on the high potential side are larger than $R_H$ and $R_3$ on the low potential side, the difference value $V_{IN}$ of the operational amplifier 56 can be reduced and the amplification factor A can be increased accordingly.

It can be seen from the formula (F7) that by configuring to satisfy a condition of m>n, the voltage $V_+$ input to the non-inverting input terminal is not lower than the voltage $V_-$ input to the inverting input terminal and the operational amplifier 56 is stably operated, so that temperature detection accuracy of the load 21 can be ensured. The power supply unit 10 according to the present embodiment is configured to satisfy the condition of m>n regardless of the temperature of the load 21 in the normal temperature range. With this configuration, the temperature of the load 21 can be detected with high accuracy regardless of the temperature of the load 21. As another embodiment, the power supply unit 10 may be configured such that the condition of m>n is satisfied only when the load 21 is in a part of the normal temperature range. Specifically, the power supply unit 10 may be configured such that the condition of m>n is satisfied when the load 21 is in the above temperature range, the above temperature range and the above first temperature, and the above temperature range and the above second temperature. With such a configuration, a width of options for the load 21 and other elements can be widened.

(Operation of Aerosol Inhaler)

An operation of the aerosol inhaler 1 configured as described above will be described with reference to FIG. 6. When the aerosol generation request is detected, the processor 55 of the MCU 50 sends a turn-on command to the switch 61, and sends a turn-off command to the switch 62. When the switch 61 is turned on and the switch 62 is turned off in response to these commands, a large current flows through the load 21 via the heating circuit, and the current flowing through the first element 63, the second element 64 and the third element 65 is zero or almost zero. Thereby, the load 21 is heated to generate the aerosol.

After a predetermined time has elapsed since a start of heating the load 21, the processor 55 sends a turn-off command to the switch 61, and sends a turn-on command to the switch 62. When the switch 61 is turned off and the switch 62 is turned on in response to these commands, a current flows through the first series circuit C1 and the second series circuit C2 via the first connection circuit. Then, a difference value ($V_{IN}$) between output signals of the first series circuit C1 and the second serial circuit C2 is amplified by the operational amplifier 56, digitally converted by the ADC 57, and input to the processor 55. The processor 55 detects the temperature of the load 21 based on the input signal from the ADC 57.

After detecting the temperature of the load 21, the processor 55 sends a turn-on command to the switch 61 and sends a turn-off command to the switch 62 to start generating the aerosol again. By repeating the above operation, the temperature of the load 21 is detected with high frequency during an aerosol generation period according to the aerosol generation request.

(Effects of Embodiment)

As described above, according to the power supply unit 10, the electric resistance value $R_H$ of the load 21 in the normal temperature range is smaller than the first electric resistance value $R_1$, the second electric resistance value $R_2$ and the third electric resistance value $R_3$. Therefore, the temperature of the load 21 can be efficiently controlled in the normal temperature range, and the aerosol can be efficiently generated.

According to the power supply unit 10, a relationship of m>n is satisfied in the normal temperature range. Therefore, in the normal temperature range, the voltage $V_+$ input to the non-inverting input terminal can be prevented from being lower than the voltage $V_-$ input to the inverting input terminal in the operational amplifier 56, and the temperature of the load 21 can be detected with high accuracy.

In the power supply unit 10, the first series circuit C1 is connected to the non-inverting input terminal of the operational amplifier 56. According to this configuration, the input voltage to the non-inverting input terminal of the operational amplifier 56 can be increased as the temperature of the load 21 is higher. Therefore, at high temperature, the voltage $V_+$ input to the non-inverting input terminal of the operational amplifier 56 is easily prevented from being lower than the voltage $V_-$ input to the inverting input terminal. Since the input voltage to the non-inverting input terminal is increased at high temperature, the input voltage can be easily distinguished from noise, and the temperature of the load 21 at high temperature can be detected with high accuracy.

According to the power supply unit 10, power supply to the first series circuit C1 and the second series circuit C2 and power supply to the load 21 via the switch 61 can be switched under the on and off control of the switch 61 and the switch 62, and aerosol generation and temperature detection of the load 21 can be appropriately switched.

In particular, during the aerosol generation, the large current can flow from the main positive bus LU to the load 21 by the heating circuit. Therefore, temperature control of the load 21 can be performed efficiently, and the aerosol generation efficiency can be improved.

In the power supply unit 10, the heating circuit is connected to a lower potential side than a connection node of the first series circuit C1 with the operational amplifier 56. According to this configuration, power loss at the connection node of the first series circuit C1 with the operational amplifier 56 can be eliminated when the current flows only through the load 21. Therefore, the aerosol generation efficiency can be further improved.

(More Preferable Form of Embodiment)

The electric resistance value of the load 21 may include a product error of the load 21 itself. This product error is at most ±10%. Therefore, it is desirable to set a value of m to be larger than n in advance in consideration of existence of such a product error.

Specifically, the value of m is set to 1.2 times or larger of n regardless of the temperature of the load 21 in the normal temperature range. This makes it possible to maintain the relationship of m>n in the normal temperature range even when the resistance temperature coefficient α of the load 21 is lowered by about 10% due to the product error. When the load 21 having a smaller product error is used, the value of m may be 1.1 times or larger or 1.05 times or larger of n regardless of the temperature of the load 21 in the normal temperature range.

In the bridge circuit including the first series circuit C1 and the second series circuit C2, at least one of the first electric resistance value $R_1$, the second electric resistance value $R_2$ and the third electric resistance value $R_3$ is preferably 1 kΩ or larger. If at least one element having an electric resistance value of 1 kΩ or larger is included, the electric resistance value of the entire bridge circuit can be sufficiently increased.

More preferably, only one or both of the second electric resistance value $R_2$ and the third electric resistance value $R_3$ among the first electric resistance value $R_1$, the second electric resistance value $R_2$ and the third electric resistance value $R_3$ are 1 kΩ or larger. Considering that the electric resistance value $R_H$ is sufficiently small and the condition of m>n is satisfied, values of n and m can be prevented from being unnecessarily large by setting only one or both of the second electric resistance value $R_2$ and the third electric resistance value $R_3$ to 1 kΩ or larger.

Since the aerosol inhaler 1 generates the aerosol by heating the load 21, it is desirable from a viewpoint of aerosol generation efficiency that an amount of current flowing through the load 21 can be sufficiently large even when the temperature of the load 21 is high. From such a viewpoint and low procurement cost, the resistance temperature coefficient α of the load 21 is preferably about 1000 [ppm/° C.] or smaller. Examples of a material of the load 21 having the resistance temperature coefficient α of 1000 [ppm/° C.] or smaller include SUS (stainless steel) having a resistance temperature coefficient α of about [1000 ppm/° C.], NiCr (nichrome) having a resistance temperature coefficient α of about [100 ppm/° C.] or the like. In order to detect the temperature of the load 21 with higher accuracy, the load 21 having the resistance temperature coefficient α of about 2000 [ppm/° C.] or smaller may be used.

In this way, by lowering the resistance temperature coefficient α of the load 21, the change in the input signal of the operational amplifier 56 with respect to the change in the temperature of the load 21 can be reduced. Therefore, the input voltage can be amplified with a large amplification factor in the operational amplifier 56, and the detection resolution of the temperature of the load 21 can be increased. In particular, a configuration in which NiCr is used for the load 21 is more preferable since the cost is low, the input signal $V_{IN}$ of the operational amplifier 56 can be minimized, and the electric resistance value at high temperature can be reduced.

(First Modification of Aerosol Inhaler)

Figure 8:
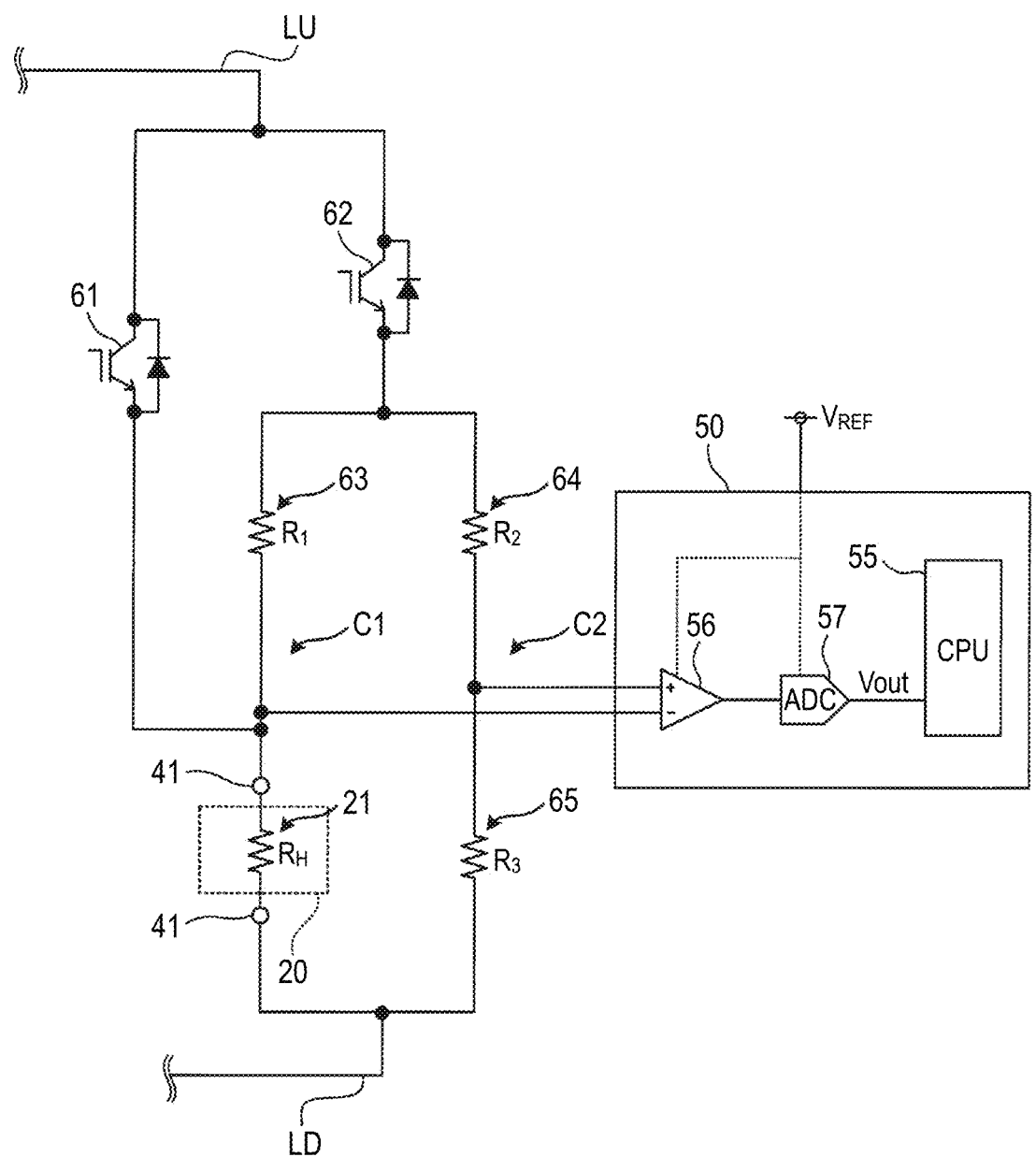
FIG. 8 is a diagram showing a first modification of the main part of the electric circuit of the power supply unit shown in FIG. 7.

FIG. 8 is a diagram showing a first modification of the main part of the electric circuit of the power supply unit 10 shown in FIG. 7. FIG. 8 shows the same configuration as that shown in FIG. 7 except that the first series circuit C1 is connected to the inverting input terminal of the operational amplifier 56 and the second series circuit C2 is connected to the non-inverting input terminal of the operational amplifier 56. Even with the configuration shown in FIG. 8, the temperature of the load 21 can be detected with high resolution.

Note that in the configuration shown in FIG. 8, the relationship between n and m described above is reversed. That is, in the configuration shown in FIG. 8, a condition of n>m is satisfied regardless of the temperature of the load 21 in the normal temperature range. With this configuration, the temperature of the load 21 can be detected with high accuracy regardless of the temperature of the load 21. In the present modification, n constitutes a first resistance ratio, and m constitutes a second resistance ratio. As another embodiment, the power supply unit 10 may be configured such that the condition of n>m is satisfied only when the load 21 is in a part of the normal temperature range. Specifically, the power supply unit 10 may be configured such that the condition of n>m is satisfied when the load 21 is in the above temperature range, the above temperature range and the above first temperature, and the above temperature range and the above second temperature. With such a configuration, a width of options for the load 21 and other elements can be widened.

(Second Modification of Aerosol Inhaler)

Figure 9:
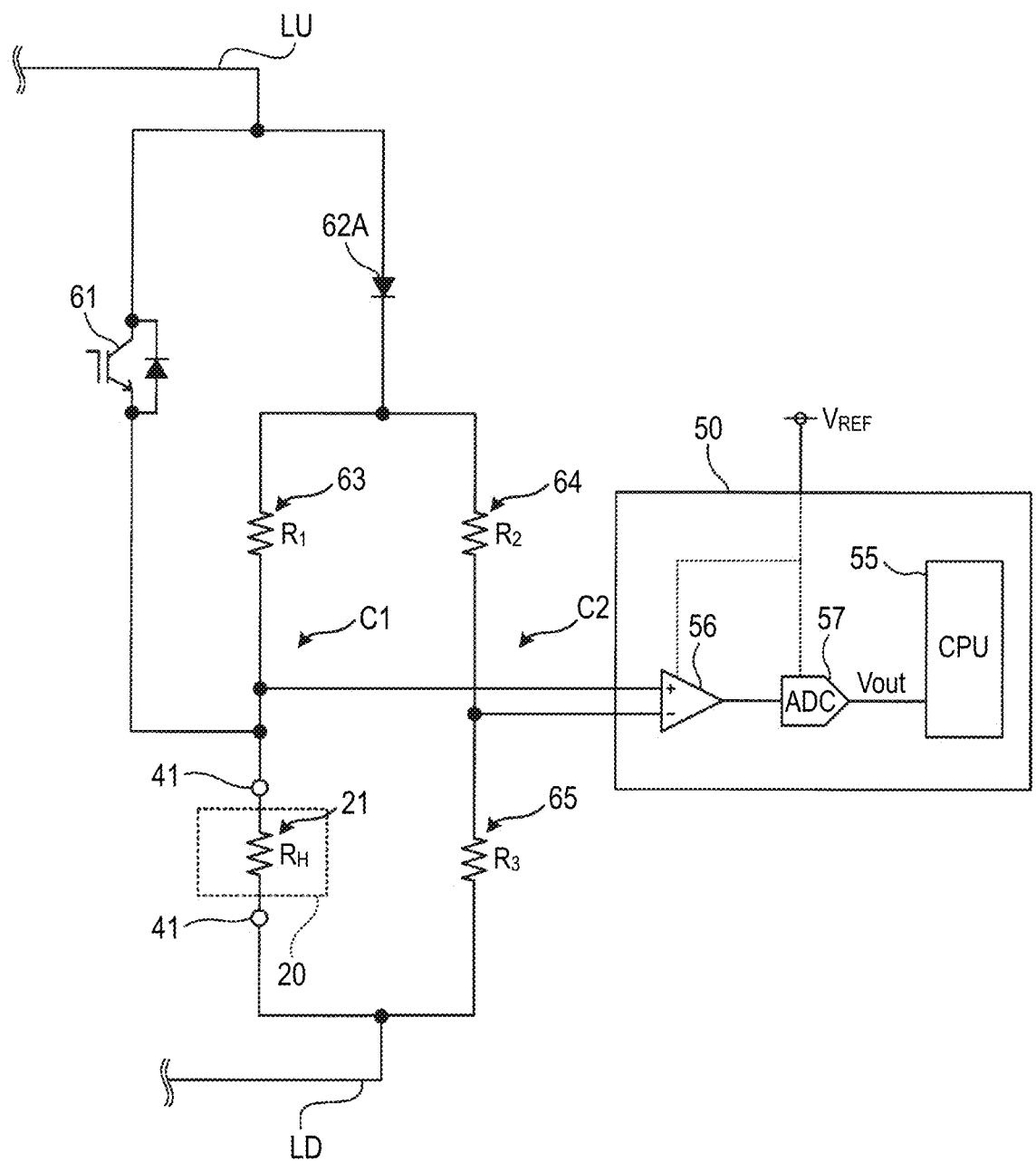
FIG. 9 is a diagram showing a second modification of the main part of the electric circuit of the power supply unit shown in FIG. 7.

FIG. 9 is a diagram showing a second modification of the main part of the electric circuit of the power supply unit 10 shown in FIG. 7. FIG. 9 shows the same configuration as that shown in FIG. 7 except that the switch 62 included in the first connection circuit is replaced with a diode 62A. The diode 62A has a forward direction from the high potential side to the low potential side, and specifically, is configured such that an anode is connected to the main positive bus LU, and a cathode is connected to the first series circuit C1 and the second series circuit C2. The diode 62A is mainly used to prevent the current from flowing from the heating circuit to the main positive bus LU.

In the present modification, when the aerosol generation request is detected, the processor 55 of the MCU 50 sends a turn-on command to the switch 61. When the switch 61 is turned on in response to the command, a current flows through the load 21 via the heating circuit, and the load 21 is heated to generate the aerosol. At this time, a node at which the first connection circuit, the first series circuit C1 and the second series circuit C2 are connected, and a node at which the heating circuit and the first series circuit C1 are connected, are equal in potential. That is, since potentials at both ends of the first element 63 are equal, no current flows through the first element 63. Therefore, when the switch 61 is in turned on, the current flows only through the heating circuit. Therefore, the load 21 can be efficiently heated. On the other hand, at the time of temperature detection, the processor 55 sends a turn-off command to the switch 61. When the switch 61 is turned off in response to the command, a current flows through the bridge circuit via the diode 62A. Therefore, the processor 55 can detect the temperature of the load 21.

According to this modification, since the switch 62 can be replaced with the diode 62A, manufacturing cost and size of the power supply unit 10 can be reduced. Since the switch on which the processor 55 can perform the on and off control is only the switch 61, calculation resource of the processor 55 can be saved. Since the combined resistance value of the bridge circuit is sufficiently larger than the electric resistance value of the load 21, the diode 62A can be omitted. By omitting the diode 62A, the cost and size can be further reduced. On the other hand, when the diode 62A is provided, a backflow of the current from the bridge circuit to the main positive bus LU can be prevented, and safety can be improved.

(Third Modification of Aerosol Inhaler)

Figure 10:
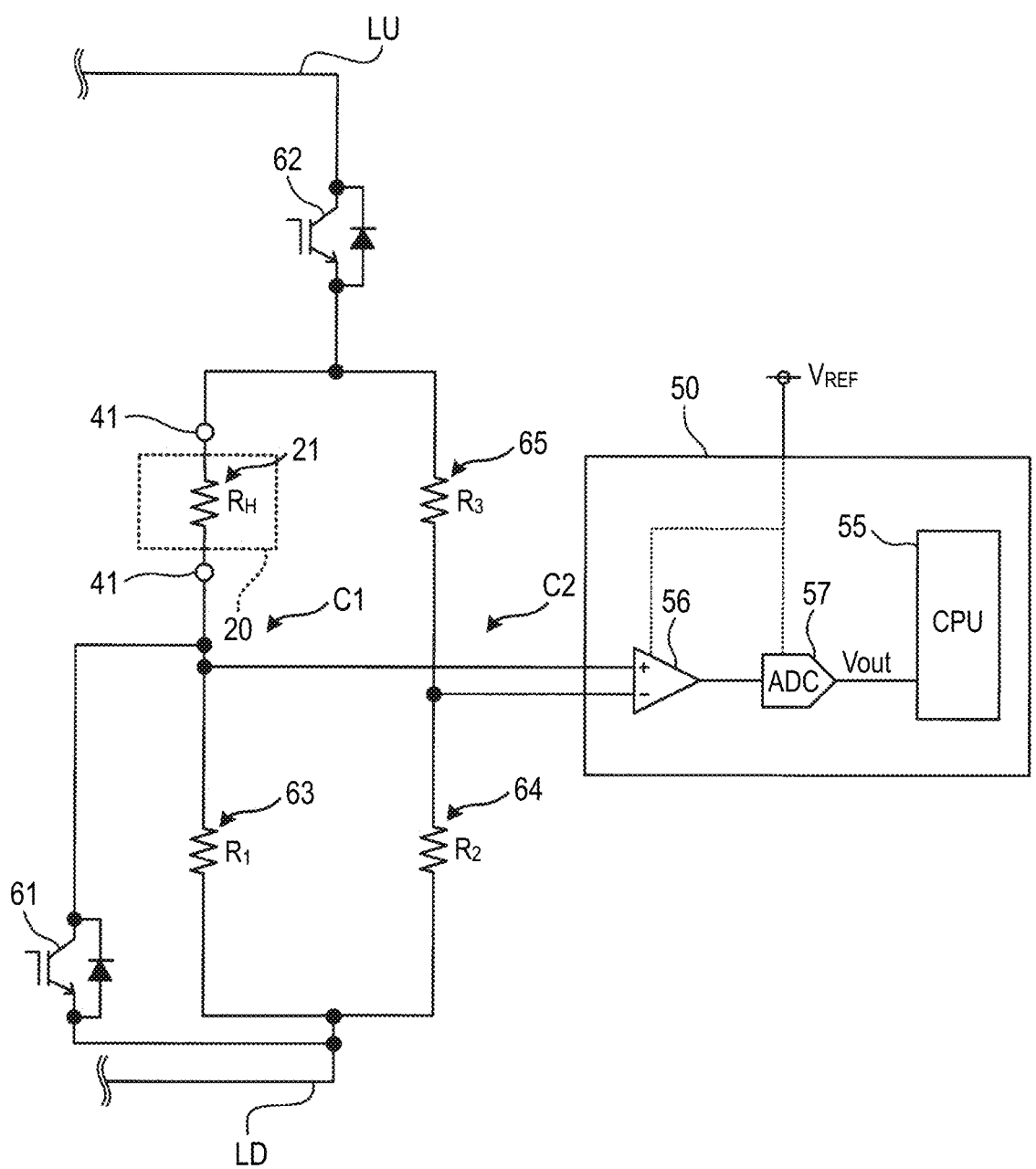
FIG. 10 is a diagram showing a third modification of the main part of the electric circuit of the power supply unit shown in FIG. 7.

FIG. 10 is a diagram showing a third modification of the main part of the electric circuit of the power supply unit 10 shown in FIG. 7. FIG. 10 shows the same configuration as that shown in FIG. 7 except that positions of the load 21 and the first element 63 are reversed in the first series circuit C1, positions of the second element 64 and the third element 65 are reversed in the second series circuit C2, and connection positions of the heating circuit including the switch 61 are changed.

The emitter of the switch 61 included in the heating circuit is connected to a higher potential side than the connection node of the first series circuit C1 with the operational amplifier 56, and the collector of the switch 61 is connected to the main negative bus LD.

In the present modification, the first series circuit C1 has a configuration in which the first element 63 is a low potential side element and the load 21 is a high potential side element. The second series circuit C2 has a configuration in which the second element 64 is a low potential side element and the third element 65 is a high potential side element. In this modification, arrangement of elements in the first series circuit C1 and the second series circuit C2 is opposite to that shown in FIG. 7. Therefore, the relationship between n and m described above is reversed, and a relationship of n>m is satisfied when the temperature of the load 21 is in the normal temperature range. As another embodiment, the power supply unit 10 may be configured such that the condition of n>m is satisfied only when the load 21 is in a part of the normal temperature range. Specifically, the power supply unit 10 may be configured such that the condition of n>m is satisfied when the load 21 is in the above temperature range, the above temperature range and the above first temperature, and the above temperature range and the above second temperature. With such a configuration, a width of options for the load 21 and other elements can be widened.

Here, a value obtained by dividing the electric resistance value $R_H$ of the high potential side load 21 in the first series circuit $C_1$ by the first electric resistance value $R_1$ of the low potential side first element 63 is 1/n, and a value obtained by dividing the third electric resistance value $R_3$ of the high potential side the third element 65 in the second series circuit $C_2$ by the second electric resistance value $R_2$ of the low potential side second element 64 is 1/m. (1/n) constitutes a second resistance ratio and (1/m) constitutes a first resistance ratio. In the present modification, since the relationship of n>m is satisfied, a relationship of (1/n)<(1/m) is satisfied.

That is, note that the relationship that the resistance ratio (the value obtained by dividing the high potential side resistance value by the low potential side resistance value) of the series circuit connected to the inverting input terminal of the operational amplifier 56 is larger than the resistance ratio (the value obtained by diving the high potential side resistance value by the low potential side resistance value) of the series circuit connected to the non-inverting input terminal of the operational amplifier 56 is the same as in FIG. 7.

In the present modification, when the aerosol generation request is detected, the processor 55 of the MCU 50 sends a turn-on command to the switches 61, 62. When the switches 61, 62 are turned on in response to the command, a current flows through the load 21 by a series circuit of the first connection circuit, the load 21 and the heating circuit, and the load 21 is heated to generate the aerosol. The electric resistance value $R_H$ of the load 21 is sufficiently smaller than the combined resistance value of the second series circuit C2. Therefore, when the switches 61, 62 are turned on, the large current can flow through the load 21. Therefore, the load 21 can be efficiently heated.

On the other hand, at the time of temperature detection, the processor 55 sends a turn-off command to the switch 61. When the switch 61 is turned off in response to the command, a current flows through the bridge circuit via the first connection circuit. Therefore, the processor 55 can detect the temperature of the load 21.

According to this modification, since the large current can flow from the main positive bus LU to the load 21 by turning on the switch 61 of the heating circuit, the aerosol generation efficiency can be improved. Since the load 21 is controlled by minus control, wiring saving can be achieved.

In the present modification, the heating circuit is connected to the higher potential side than the connection node of the first series circuit C1 with the operational amplifier 56. According to this configuration, there is no power loss at the connection node of the first series circuit C1 with the operational amplifier 56 when the current flows only through the load 21. Therefore, the aerosol generation efficiency can be further improved.

In FIG. 10, the connection position of the collector of the switch 61 with the first series circuit C1 can be on a lower potential side than the connection node of the first series circuit C1 with the operational amplifier 56.

In FIG. 10, the switch 62 can be replaced with a diode whose forward direction is from the high potential side to the low potential side. In this case, when the switch 61 is turned off, a current can flow through the first series circuit C1 and the second series circuit C2. On the other hand, when the switch 61 is turned on, the current can preferentially flow through the load 21 whose electric resistance value is sufficiently smaller than that of the second series circuit C2. The circuit can also be protected by the diode.

(Fourth Modification of Aerosol Inhaler)

Figure 11:
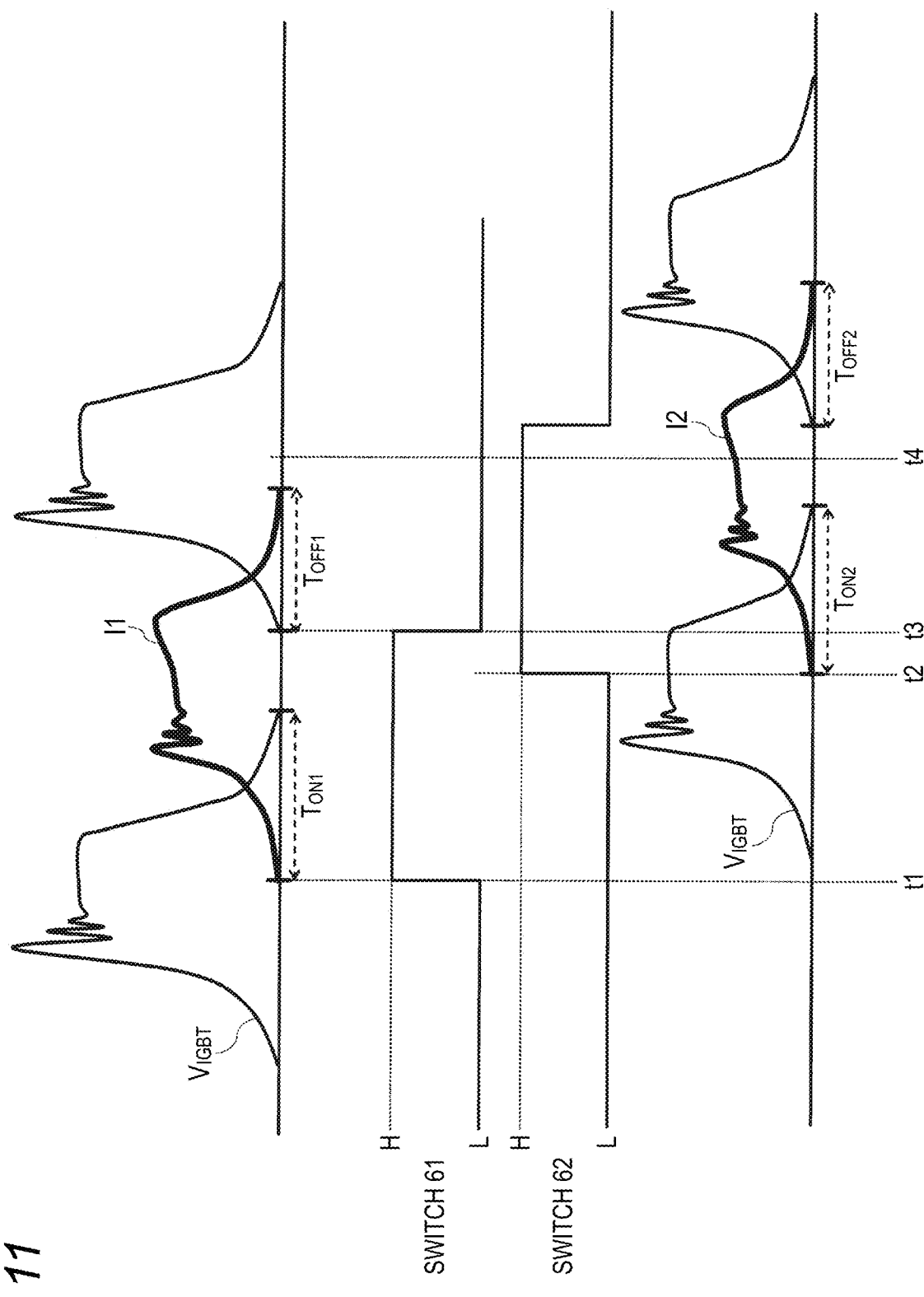
FIG. 11 is a diagram showing a timing chart for explaining a modification of an operation of the aerosol inhaler including the power supply unit whose main part configuration is shown in FIG. 7 or 8.

FIG. 11 is a diagram showing a timing chart for explaining a modification of the operation of the aerosol inhaler 1 including the power supply unit 10 whose main part configuration is shown in FIG. 7 or 8. FIG. 11 shows the timing chart of a period from a start of the aerosol generation in response to the aerosol generation request to an end of the temperature detection of the load 21. FIG. 11 shows command signals of the switches 61, 62 during this period. In FIG. 11, a waveform of a collector current I1 of the switch 61 and a waveform of a collector-emitter voltage $V_{IGBT}$ are shown above a waveform of the command signal of the switch 61. In FIG. 11, a waveform of a collector current I2 of the switch 62 and a waveform of a collector-emitter voltage $V_{IGBT}$ are shown below a waveform of the command signal of the switch 62.

When the aerosol generation request is detected, the processor 55 of the MCU 50 sends a turn-on command (H) to the switch 61 at a timing t1. At the timing t1, a turn-off command (L) is sent to the switch 62. When the switch 61 is turned on in response to the turn-on command at the timing t1, a current I1 starts to flow through the load 21 via the heating circuit, and the load 21 is heated to start the aerosol generation. As shown in an upper part of FIG. 11, the current I1 is stabilized at a desired value after a predetermined turn-on time $T_{ON1}$ has elapsed since the switch 61 is turned on.

At a timing after the turn-on time $T_{ON1}$ has elapsed since the timing t1 and when a timing t2 is reached during a turn-on period of the switch 61, the processor 55 sends an the command (H) to the switch 62. When the switch 62 is turned on in response to the command, the current I2 starts to flow through the first series circuit C1 and the second series circuit C2 via the first connection circuit. As shown in a lower part of FIG. 11, the current I2 is stabilized at a desired value after a predetermined turn-on time $T_{ON2}$ has elapsed since the switch 62 is turned on.

After the timing t2, at a timing t3 sufficiently before the turn-on time $T_{ON2}$ elapses, the processor 55 sends the turn-off command (L) to the switch 61. When the switch 61 is turned off in response to the command, supply of the current I1 to the load 21 via the heating circuit is stopped. The current I1 at this time decreases over a predetermined turn-off time $T_{OFF1}$.

The processor 55 captures an output signal of the ADC 57 at a timing during a turn-on period of the switch 62, at a timing t4 after the turn-on time $T_{ON2}$ has elapsed since the timing t2 and the turn-off time $T_{OFF1}$ has elapsed since the timing t3, and detects the temperature of the load 21 based on this output signal. After the temperature is detected, the processor 55 sends a turn-off command to the switch 62. In response to this command, the switch 62 is turned off to return to an initial state of the timing chart. The number of times the processor 55 detects the temperature of the load 21 during the turn-on period of the switch 62 may be larger than one. In such a case, the temperature of the load 21 may be obtained from an average value or a median value of a plurality of output signals of the ADC 57 and a plurality of detected temperatures.

As described above, in the present modification, the processor 55 is configured to send the turn-on command to the switch 62 while the switch 61 is turned on. According to this configuration, the power supply to the first series circuit C1 and the second series circuit C2 and the power supply to the load 21 via the heating circuit can be efficiently switched. As a result, the temperature of the load 21 can be detected with high frequency even during the aerosol generation period.

In the present modification, the processor 55 executes temperature detection processing on the load 21 based on an output of the operational amplifier 56 at the timing t4 after the turn-on time $T_{ON2}$ has elapsed since the timing t2 and after the turn-off time $T_{OFF1}$ has elapsed since the timing t3. According to this configuration, the temperature detection processing on the load 21 can be performed when the supply of the current to the load via the heating circuit is almost eliminated. Therefore, the accuracy of this processing can be improved.

Although the first cartridge 20 including the load 21 is configured to be attachable to and detachable from the power supply unit 10 in the above embodiment and modifications, the first cartridge 20 including the load 21 may be integrated with the power supply unit 10.

The present specification describes at least the following matters. Although the corresponding constituent elements or the like in the above embodiment are shown in parentheses, the present disclosure is not limited thereto.

(1) A power supply unit (power supply unit 10) for an aerosol inhaler (aerosol inhaler 1) having a power supply (power supply 12) capable of performing discharge to a load (load 21), which heats an aerosol generation source and whose temperature and electric resistance value (electric resistance value $R_H$) have a correlation, the power supply unit for the aerosol inhaler includes:

a first element (first element 63) having a first electric resistance value (first electric resistance value $R_1$) connected in series to the load;

a second series circuit (second series circuit C2) including a second element (second element 64) having a second electric resistance value (second electric resistance value $R_2$) and a third element (third element 65) having a third electric resistance value (third electric resistance value $R_3$) connected in series to the second element, and connected in parallel with a first series circuit (first series circuit C1) including the load and the first element; and an operational amplifier (operational amplifier 56) in which one of a non-inverting input terminal and an inverting input terminal is connected to the first series circuit, and the other of the non-inverting input terminal and the inverting input terminal is connected to the second series circuit.

Each of the first electric resistance value, the second electric resistance value and the third electric resistance value is larger than the electric resistance value of the load at a temperature in a normal temperature or a predetermined temperature range.

According to (1), since the electric resistance value of the load at the normal temperature or the temperature in the temperature range is smaller than the first electric resistance value, the second electric resistance value and the third electric resistance value, the temperature of the load can be efficiently controlled during the discharge at the normal temperature or in the temperature range, and aerosol can be efficiently generated. In addition, since a voltage input to the operational amplifier can be reduced with low noise, the temperature of the load can be detected with high resolution by using a signal amplified by increasing an amplification factor of the operational amplifier.

(2) In the power supply unit for the aerosol inhaler according to (1), each of the first electric resistance value, the second electric resistance value and the third electric resistance value is larger than the electric resistance value of the load at a temperature at which the aerosol is generated from the aerosol generation source.

According to (2), even when the temperature of the load is increased due to aerosol generation, a relationship that the electric resistance value of the load is smaller than the first electric resistance value, the second electric resistance value and the third electric resistance value is satisfied. Therefore, the temperature of the load can be detected with high accuracy even at high temperature, while aerosol generation efficiency can be improved.

(3) In the power supply unit for the aerosol inhaler according to (1), each of the first electric resistance value, the second electric resistance value and the third electric resistance value is larger than the electric resistance value of the load at a temperature that is reached only when the aerosol generation source is exhausted.

According to (3), even when the aerosol generation source is exhausted and the temperature of the load is increased, the relationship that the electric resistance value of the load is smaller than the first electric resistance value, the second electric resistance value and the third electric resistance value is satisfied. Therefore, the temperature of the load can be detected with high accuracy even at high temperature.

(4) In the power supply unit for the aerosol inhaler according to any one of (1) to (3), at least one of the first electric resistance value, the second electric resistance value and the third electric resistance value is 1 kΩ or larger.

According to (4), when a current flows through the first series circuit and the second series circuit, an amount of heat generated in a circuit including the first series circuit and the second series circuit can be reduced. As a result, the temperature of the load can be prevented from being affected by the current, and the temperature of the load can be detected with high accuracy. In addition, power consumption when detecting the temperature of the load can be reduced.

(5) In the power supply unit for the aerosol inhaler according to (4), only one or both of the second electric resistance value and the third electric resistance value among the first electric resistance value, the second electric resistance value and the third electric resistance value are 1 kΩ or larger.

According to (5), an electric resistance value of the entire circuit including the first series circuit and the second series circuit can be set to an appropriate value, and manufacturing cost can be reduced and design flexibility can be improved.

(6) In the power supply unit for the aerosol inhaler according to (1), a condition that a first resistance ratio (m, n or 1/m), is larger than a second resistance ratio (n, m or 1/n) is satisfied when the temperature of the load is in the temperature range. The first resistance ratio is a value obtained by dividing an electric resistance value of a high potential side element in a circuit connected to the inverting input terminal of the operational amplifier among the first series circuit and the second series circuit by an electric resistance value of a low potential side element. The second resistance ratio is a value obtained by dividing an electric resistance value of a high potential side element in a circuit connected to the non-inverting input terminal of the operational amplifier among the first series circuit and the second series circuit by an electric resistance value of a low potential side element.

According to (6), since a voltage $V_+$ input to the non-inverting input terminal can be prevented from being lower than a voltage $V_-$ input to the inverting input terminal in the operational amplifier, the temperature of the load can be detected with high accuracy while the operational amplifier can be protected.

(7) In the power supply unit for the aerosol inhaler according to (6), the condition is satisfied when the load is at a temperature at which aerosol can be generated from the aerosol generation source.

According to (7), the voltage $V_+$ input to the non-inverting input terminal can be prevented from being lower than the voltage $V_-$ input to the inverting input terminal in the operational amplifier even when the aerosol is generated. Therefore, the temperature of the load can be detected with high accuracy while the operational amplifier can be protected even at high temperature.

(8) In the power supply unit for the aerosol inhaler according to (6), the condition is satisfied when the load is at a temperature that can be reached only when the aerosol generation source is exhausted.

According to (8), the voltage $V_+$ input to the non-inverting input terminal can be prevented from being lower than the voltage $V_-$ input to the inverting input terminal in the operational amplifier even when the aerosol generation source is exhausted. Therefore, the temperature of the load can be detected with high accuracy while the operational amplifier can be protected even at high temperature.

(9) In the power supply unit for the aerosol inhaler according to (6), the first resistance ratio is equal to or larger than 1.2 times the second resistance ratio, when the temperature of the load is in the temperature range.

According to (9), the voltage $V_+$ input to the non-inverting input terminal can be prevented from being lower than the voltage $V_-$ input to the inverting input terminal in the operational amplifier even when the electric resistance value of the load is lowered by 10% due to a product error of the load.

(10) In the power supply unit for the aerosol inhaler according to any one of (1) to (9), the first series circuit is connected to the non-inverting input terminal of the operational amplifier.

According to (10), as the temperature of the load is higher, the input voltage to the non-inverting input terminal of the operational amplifier can be increased. Therefore, the voltage $V_+$ input to the non-inverting input terminal can be prevented from being lower than the voltage $V_-$ input to the inverting input terminal in the operational amplifier even at high temperature, and the temperature of the load can be detected with high accuracy while the operational amplifier can be protected even at high temperature. In addition, since the input voltage to the non-inverting input terminal is increased at high temperature, the input voltage can be easily distinguished from noise, and the temperature of the load at high temperature can be detected with high accuracy.

(11) In the power supply unit for the aerosol inhaler according to any one of (1) to (9), the load has a resistance temperature coefficient of 1000 [ppm/° C.] or smaller.

According to (11), since the resistance temperature coefficient of the load is low, a change in the input voltage to the operational amplifier with respect to a change in the resistance of the load is small. Therefore, the input voltage can be amplified with a large amplification factor in the operational amplifier, and the detection resolution of the temperature of the load can be increased.

(12) In the power supply unit for the aerosol inhaler according to any one of (1) to (9), the load contains NiCr.

According to (12), since the resistance temperature coefficient of the load is low, a change in the input voltage to the operational amplifier with respect to a change in the resistance of the load is small. Therefore, the input voltage can be amplified with a large amplification factor in the operational amplifier, and the detection resolution of the temperature of the load can be increased. In addition, since the electric resistance value of the load is not excessively high even when the aerosol is generated, the aerosol generation efficiency can be maintained.

(13) A power supply unit (power supply unit 10) for an aerosol inhaler (aerosol inhaler 1) having a power supply (power supply 12) capable of performing discharge to a load (load 21), which heats an aerosol generation source and whose temperature and electric resistance value (electric resistance value $R_H$) have a correlation, the power supply unit for the aerosol inhaler includes:

a first element (first element 63) having a first electric resistance value (first electric resistance value $R_1$) connected in series to the load;

a second series circuit (second series circuit C2) including a second element (second element 64) having a second electric resistance value (second electric resistance value $R_2$) and a third element (third element 65) having a third electric resistance value (third electric resistance value $R_3$) connected in series to the second element, and connected in parallel with a first series circuit (first series circuit C1) including the load and the first element; and an operational amplifier (operational amplifier 56) in which one of a non-inverting input terminal and an inverting input terminal is connected to the first series circuit, and the other of the non-inverting input terminal and the inverting input terminal is connected to the second series circuit.

When the load is at least one of a normal temperature or a temperature in a predetermined temperature range, a first temperature at which an aerosol is generated, and a second temperature that is reached only when the aerosol generation source is exhausted, a first resistance ratio (m, n or 1/m), which is a value obtained by dividing an electric resistance value of a high potential side element in a circuit connected to the inverting input terminal of the operational amplifier among the first series circuit and the second series circuit by an electric resistance value of a low potential side element, is larger than a second resistance ratio (n, m or 1/n), which is a value obtained by dividing an electric resistance value of a high potential side element in a circuit connected to the non-inverting input terminal of the operational amplifier among the first series circuit and the second series circuit by an electric resistance value of a low potential side element.

According to (13), since the voltage input to the operational amplifier can be reduced with low noise, the amplification factor of the operational amplifier can be increased, and the temperature of the load can be detected with high resolution by using an amplified signal. Further, since the voltage $V_+$ input to the non-inverting input terminal can be prevented from being lower than the voltage $V_-$ input to the inverting input terminal in the operational amplifier, the temperature of the load can be detected with high accuracy.

What is claimed is:

1. An aerosol inhaler comprising:
a load configured to heat an aerosol generation source, wherein a temperature and electric resistance value of the load have a correlation;
a power supply configured to discharge to the load;
a first element connected in series to the load and having a first electric resistance value;
a second series circuit including a second element having a second electric resistance value and a third element connected in series to the second element and having a third electric resistance value, and connected in parallel with a first series circuit including the load and the first element; and
an operational amplifier in which one of a non-inverting input terminal and an inverting input terminal is connected to the first series circuit, and the other of the non-inverting input terminal and the inverting input terminal is connected to the second series circuit, wherein
each of the first electric resistance value, the second electric resistance value and the third electric resistance value is larger than the electric resistance value of the load at a temperature at which aerosol is generated form the aerosol generation source,
a condition that a first resistance ratio is larger than a second resistance ratio is satisfied when the load is at the temperature at which aerosol is generated from the aerosol generation source,
the first resistance ratio is a value obtained by dividing an electric resistance value of a high potential side element in a circuit connected to the inverting input terminal of the operational amplifier among the first series circuit and the second series circuit by an electric resistance value of a low potential side element, and
the second resistance ratio is a value obtained by dividing an electric resistance value of a high potential side element in a circuit connected to the non-inverting input terminal of the operational amplifier among the first series circuit and the second series circuit by an electric resistance value of a low potential side element.

2. The aerosol inhaler according to claim 1, wherein
at least one of the first electric resistance value, the second electric resistance value and the third electric resistance value is 1 kΩ or larger.

3. The aerosol inhaler according to claim 2, wherein
only one or both of the second electric resistance value and the third electric resistance value among the first electric resistance value, the second electric resistance value and the third electric resistance value are 1 kΩ or larger.

4. The aerosol inhaler according to claim 1, wherein the first resistance ratio is equal to or larger than 1.2 times the second resistance ratio, when the temperature of the load is in the temperature range.

5. The aerosol inhaler according to claim 1, wherein the first series circuit is connected to the non-inverting input terminal of the operational amplifier.

6. The aerosol inhaler according to claim 1, wherein the load has a resistance temperature coefficient of 1000 ppm/° C. or smaller.

7. The aerosol inhaler according to claim 1, wherein the load contains NiCr.

8. An aerosol inhaler comprising:

a load configured to heat an aerosol generation source, wherein a temperature and electric resistance value of the load have a correlation;

a power supply configured to discharge to the load;

a first element connected in series to the load and having a first electric resistance value;

a second series circuit including a second element having a second electric resistance value and a third element connected in series to the second element and having a third electric resistance value, and connected in parallel with a first series circuit including the load and the first element to the power supply; and an operational amplifier in which one of a non-inverting input terminal and an inverting input terminal is connected to the first series circuit, and the other of the non-inverting input terminal and the inverting input terminal is connected to the second series circuit, wherein when the load is at a temperature in a predetermined temperature range, a first temperature at which an aerosol is generated, and a second temperature that is reached only when the aerosol generation source is exhausted, a first resistance ratio, which is a value obtained by dividing an electric resistance value of a high potential side element in a circuit connected to the inverting input terminal of the operational amplifier among the first series circuit and the second series circuit by an electric resistance value of a low potential side element, is larger than a second resistance ratio, which is a value obtained by dividing an electric resistance value of a high potential side element in a circuit connected to the non-inverting input terminal of the operational amplifier among the first series circuit and the second series circuit by an electric resistance value of a low potential side element.

9. An aerosol inhaler comprising:

a load configured to heat an aerosol generation source, wherein a temperature and electric resistance value of the load have a correlation;

a power supply configured to discharge to the load;

a first element connected in series to the load and having a first electric resistance value;

a second series circuit including a second element having a second electric resistance value and a third element connected in series to the second element and having a third electric resistance value, and connected in parallel with a first series circuit including the load and the first element; and an operational amplifier in which one of a non-inverting input terminal and an inverting input terminal is connected to the first series circuit, and the other of the non-inverting input terminal and the inverting input terminal is connected to the second series circuit, wherein each of the first electric resistance value, the second electric resistance value and the third electric resistance value is larger than the electric resistance value of the load at a temperature that is reached only when the aerosol generation source is exhausted, a condition that a first resistance ratio is larger than a second resistance ratio is satisfied when the load is at the temperature that is reached only when the aerosol generation source is exhausted, the first resistance ratio is a value obtained by dividing an electric resistance value of a high potential side element in a circuit connected to the inverting input terminal of the operational amplifier among the first series circuit and the second series circuit by an electric resistance value of a low potential side element, and the second resistance ratio is a value obtained by dividing an electric resistance value of a high potential side element in a circuit connected to the non-inverting input terminal of the operational amplifier among the first series circuit and the second series circuit by an electric resistance value of a low potential side element.

10. The aerosol inhaler according to claim 9, wherein at least one of the first electric resistance value, the second electric resistance value and the third electric resistance value is 1 kΩ or larger.

11. The aerosol inhaler according to claim 10, wherein only one or both of the second electric resistance value and the third electric resistance value among the first electric resistance value, the second electric resistance value and the third electric resistance value are 1 kΩ or larger.

12. The aerosol inhaler according to claim 9, wherein the first resistance ratio is equal to or larger than 1.2 times the second resistance ratio, when the temperature of the load is in the temperature range.

13. The aerosol inhaler according to claim 9, wherein the first series circuit is connected to the non-inverting input terminal of the operational amplifier.

14. The aerosol inhaler according to claim 9, wherein the load has a resistance temperature coefficient of 1000 ppm/° C. or smaller.

15. The aerosol inhaler according to claim 9, wherein the load contains NiCr.

* * * * *